(12) United States Patent
Heil et al.

(10) Patent No.: US 6,919,470 B2
(45) Date of Patent: Jul. 19, 2005

(54) ARYL AND HETEROARYL SULFONATES

(75) Inventors: Markus Heil, Leichlingen (DE); Heinrich Meier, Wuppertal (DE); Paul Naab, Wuppertal (DE); Arnd Voerste, Cologne (DE); Jean-Marie-Viktor de Vry, Rosrath (DE); Dirk Denzer, Solingen (DE); Frank Mauler, Overath (DE); Klemens Lustig, Wuppertal (DE); Volker Hinz, Cologne (DE); Swen Allerheiligen, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/240,464

(22) PCT Filed: Mar. 19, 2001

(86) PCT No.: PCT/EP01/03119

§ 371 (c)(1),
(2), (4) Date: May 12, 2003

(87) PCT Pub. No.: WO01/74763

PCT Pub. Date: Oct. 11, 2001

(65) Prior Publication Data

US 2003/0232802 A1 Dec. 18, 2003

(30) Foreign Application Priority Data

Mar. 30, 2000 (DE) .......................... 100 15 866

(51) Int. Cl.$^7$ .............................................. C07C 309/63
(52) U.S. Cl. ................................................. 558/54
(58) Field of Search ........................................ 558/54

(56) References Cited

U.S. PATENT DOCUMENTS

| | | | | |
|---|---|---|---|---|
| 3,346,612 A | 10/1967 | Hansen | ....................... | 260/456 |
| 4,582,837 A | 4/1986 | Hauel et al. | ................. | 514/303 |
| 6,262,112 B1 | 7/2001 | Mittendorf et al. | ......... | 514/517 |
| 6,469,054 B1 | 10/2002 | Mittendorf et al. | ......... | 514/470 |
| 6,545,050 B1 | 4/2003 | Mittendorf et al. | ......... | 514/570 |

FOREIGN PATENT DOCUMENTS

| | | |
|---|---|---|
| DE | 1173720 | 7/1964 |
| EP | 0098448 | 1/1984 |
| WO | 9206962 | 4/1992 |
| WO | 9315074 | 8/1993 |
| WO | 9405633 | 3/1994 |
| WO | 9837061 | 8/1998 |
| WO | 0010967 | 3/2000 |
| WO | 0010968 | 3/2000 |

OTHER PUBLICATIONS

Skrypnik et al (1977): STN International CAPLUS database, Columbus (Ohio), Accession No., 1977:438400.*
Kametani et al (1964): STN International CAPLUS database, Columbus (Ohio), Accession No., 1964:404043.*
Hahn et al (1964): STN International, CA PLUS database (Columbus, Ohio), document No. 61:83974.*
Lipshutz, B., Buzard, D., Vivian, R., "Reductions of Aryl Perfluorosulfonates With Dimethylamine Borane (Me$_2$NH˙BH$_3$) Catalyzed By Pd(0): An Operationally Simple, Inexpensive, and General Protocol", Tetrahedron Letters, 40:6871–6874 (1999).
Rottlander, M., Knochel, P., "Palladium–Catalyzed Cross–Coupling Reactions With Aryl Nonaflates: A Practical Alternative to Aryl Triflates", J. Org. Chem., 63: 203–208 (1998).
Chem. Abstr., 109(9): 73152 (1988), Oyama, H., and Shimozono, T., "Preparation of (alkylsulfonyloxyflourophenyl) hydrazines as intermediates for herbicides and their process", Jpn. Kokai Tokkyo Koho, JP 6341,448 [88 41,448].
Chem. Abstr., 61(12): 14586h (1964), Hahn, W., Bartnik, R., and Roman, S., "Derivatives of 1,2–diphenyl–1–[p–(β–diethylamino)ethoxyphenyl]ethanol and 1,2–diphenyl–1–[p–(β–diethylamino)thioethoxyphenyl]ethanol", PL 47 973 A, Feb. 4, 1964.
Chem. Abstr., 87(5): 38400 (1977), Skrypnik, Y. G., Korotkikh, L., M., Panov, E. P., Belogurova, N. V., Vizgert, R. V., "Kenetics of alkaline hydrolysis of phenyl esters of butanesulfonic acids. Mechanism of alkaline hydrolysis of phenyl alkanesulfonates", Zh. Org. Khim., 13(2):343–346 (1977).
Chem. Abstr. 71(15): 70535t ((1969), Galoyan, G. A., Agbalyan, S. G., Esayan, G. T., "Reactions of heterocyclic compounds containing enolizing carbonyl groups. IV. Reaction of 1–phenyl–3–methyl–5–pyrazolone and 1–phenyl–5–methyl–3–pyrazolone with sulfonyl chlorides", Arm. Khim. Zh., 22(5): 430–433 (1969).
Lipshutz, B. H., Buzard, D. J., and Yun, C. S., "Pd(0)–Mediated Couplings of Aryl Nonaflates and Triflates with Diphenylphosphine–Borane. Preparation of BH$_3$–Stabilized, Unsymmetrical Triarylphosphines", Tetrahedron Letters, 40:201–204 (1999).

* cited by examiner

*Primary Examiner*—Golam M M Shameem
(74) *Attorney, Agent, or Firm*—Susan M. Pellegrino

(57) ABSTRACT

The invention relates to novel aryl and heteroaryl sulfonates of formula (Ia) and to methods for producing them and to novel aryl and heteroaryl sulfonates of formula (I) for treating and/or preventing diseases, especially for treating pain and neurodegenerative diseases, A representing (C$_6$–C$_{10}$)-aryl or 5–10-membered heteroaryl, D representing (C$_6$–C$_{10}$)-arylene or 5–10-membered heteroarylene, R$^1$ representing (C$_4$–C$_8$)-alkyl, (C$_2$–C$_8$)-alkyl, the carbon chain being interrupted by one or two heteroatoms or groups chosen from the following group: —O—, —S—, —SO— and —SO$_2$—, (C$_2$–C$_8$)-alkenyl or (C$_2$–C$_8$)-alkinyl, in formula (Ia); and R$^1$ representing (C$_3$–C$_8$)-alkyl, (C$_2$–C$_8$)-alkyl, the carbon chain being interrupted by one or two heteroatoms or groups chosen from the following group: —O—, —S—,—SO— and —SO$_2$—, (C$_2$–C$_8$)-alkenyl or (C$_2$–C$_8$)-alkinyl.

4 Claims, No Drawings

ARYL AND HETEROARYL SULFONATES

The invention relates to novel aryl and heteroaryl sulfonates and processes for their preparation, and to novel aryl and heteroaryl sulfonates for the treatment and/or prophylaxis of disorders, in particular for the treatment of states of pain and neurodegenerative disorders.

$\Delta^9$-Tetrahydrocannabinol ($\Delta^9$-THC) and, to a small extent, also $\Delta^8$-THC are the biologically active constituents in extracts of the plant *Cannabis sativa* (marijuana, hashish) and are responsible for the effects on the human central nervous system (CNS). Potential historical and contemporary therapeutic applications of *cannabis* products comprise inter alia analgesia, emesis, anorexia, glaucoma and movement disorders.

To date, two subtypes of cannabinoid receptors and one splice variant have been identified. The CB1 receptor and the splice variant CB1a are mainly localized in the central nervous system. The CB2 receptor has been found mainly in the peripheral tissue, especially in leucocytes, spleen and macrophages.

CB1 and CB2 receptors have seven transmembrane regions and belong to the family of G protein receptors. Both receptors are negatively coupled via $G_i/G_o$ protein to adenylate cyclase and possibly negatively coupled to the presynaptic release of glutamate. CB1 receptors are in addition positively coupled with potassium channels and negatively coupled with N- and Q-type calcium channels.

Several classes of structures have been disclosed to date for CB1 receptor agonists: classical cannabinoids such as, for example, $\Delta^9$-THC, nonclassical cannabinoids, aminoalkylindoles and eicosanoids. The latter includes the endogenous CB1 receptor agonist anandamide.

WO-A-98/37061, WO-A-00/10967 and WO-A-00/10968 describe substituted aryloxy-phenolsulfonic esters and their effect as cannabinoid receptor agonists.

EP-A-0 098 448 discloses substituted imidazol-2-ylphenolalkanesulfonic esters and their effect on the contractility of the heart.

Derivatives of imidazolyl- and pyrazolyl-phenol sulfonic esters and their herbicidal and pesticidal effect are disclosed in WO-A-92/06962, WO-A-93/15074 and WO-A-94/05633.

U.S. Pat. No. 3,346,612 discloses perfluorooctanesulfonic esters of 2- and 4-hydroxy-biphenyl as flame retardants.

Certain substituted phenol nonafluorobutanesulfonic esters and butanesulfonic esters are disclosed in the synthesis publications *J. Org. Chem.* 1998, 63, 203–208 and *Tetrahedr. Lett.* 1999, 40, 6871–6874.

The present invention relates to compounds of the general formula (I),

$$\text{A-D-O}-SO_2-R^1 \qquad (I)$$

in which

A represents ($C_6$–$C_{10}$)-aryl or heteroaryl with 5 to 10 ring atoms,
  where adjacent ring atoms in aryl and heteroaryl are, where appropriate, connected by a saturated or partially unsaturated bridge comprising 3 to 7 bridge atoms selected from the group of carbon, nitrogen, oxygen and sulfur, and
  where aryl, heteroaryl and the bridge are optionally substituted one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl, ($C_3$–$C_8$)-cycloalkyl, halogen, nitro, cyano, hydroxyl, trifluoromethoxy, —$CO_2R^2$, —$CONR^3R^4$, —$SO_2NR^5R^6$, —$NR^7COR^8$, —$NR^9SO_2R^{10}$, and —$NR^{11}R^{12}$, where ($C_1$–$C_8$)-alkyl in turn is optionally substituted by halogen, cyano, hydroxyl or —$NR^{13}R^{14}$,
  in which
  $R^2, R^3, R^4, R^5, R^6, R^7, R^8, R^9, R^{10}, R^{11}, R^{12}, R^{13}$ and $R^{14}$ are identical or different and denote hydrogen, optionally hydroxyl- or ($C_1$–$C_4$)-alkoxy-substituted ($C_1$–$C_8$)-alkyl or ($C_3$–$C_8$)-cycloalkyl, D represents ($C_6$–$C_{10}$)-arylene or heteroarylene with 5 to 10 ring atoms, where arylene and heteroarylene are optionally substituted, one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl, ($C_3$–$C_8$)-cycloalkyl, halogen, nitro, cyano, hydroxyl, trifluoromethyl, trifluoromethoxy and —$CO_2R^{15}$,
  in which
  $R^{15}$ denotes hydrogen, ($C_1$–$C_8$)-alkyl or ($C_3$–$C_8$)-cycloalkyl, and $R^1$ represents ($C_4$–$C_8$)-alkyl,
  represents ($C_2$–$C_8$)-alkyl where the carbon chain is interrupted by one or two heteroatoms or groups selected from the group of —O—, —S—, —SO— and —$SO_2$—,
  represents ($C_2$–$C_8$)-alkenyl, or
  represents ($C_2$–$C_8$)-alkinyl,
  where alkyl, alkenyl and alkinyl are optionally substituted one or more times by halogen and/or cyano, and the salts thereof,
with the exception of
  compounds of the general formula (I), in which D is phenylene and $R^1$ is 1,1,2,2,3,3,4,4,4-nonafluorobutyl, and
with the exception of
  [1,1'-biphenyl]-4-yl 1,1,2,2,3,3,4,4,5,5,6,6,7,7,8,8,8-heptadecafluoro-1-octanesulfonate and
  [1,1'-biphenyl]-2-yl 1,1,2,2,3,3,4,4,5,5,6,6,7,7,8,8,8-heptadecafluoro-1-octanesulfonate.

The compounds according to the invention may exist in stereoisomeric forms which either are related as image and mirror image (enantiomers) or are not related as image and mirror image (diastereomers). The invention relates to the enantiomers or diastereomers or respective mixtures thereof. These mixtures of enantiomers and diastereomers can be separated into stereoisomerically uniform components in a known manner.

The compounds according to the invention may also be in the form of their salts. Reference may generally be made here to salts with organic or inorganic bases or acids.

For the purposes of the present invention, physiologically acceptable salts are preferred. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention. Particularly preferred examples are sodium, potassium, magnesium or calcium salts, and ammonium salts derived from ammonia or organic amines such as, for example, ethylamine, di- and triethylamine, di- and triethanolamine, dicyclohexylamine, dimethylaminoethanol, arginine, lysine, ethylenediamine or 2-phenylethylamine.

The present invention also includes ammonium compounds which can be prepared by converting the free amines by alkylation.

The compounds according to the invention may also be in the form of their hydrates and/or solvates.

For the purposes of the present invention, the substituents generally have the following meaning:

($C_6$–$C_{10}$)-Ayl represents for the purposes of the invention a monovalent aromatic radical with 6 to 10 carbon atoms. Preferred aryl radicals are phenyl and naphthyl.

($C_6$–$C_{10}$)-Arylene represents for the purposes of the invention a divalent aromatic radical with 6 to 10 carbon atoms. Examples which may be mentioned are: benzene-1,2-diyl, benzene-1,3-diyl, benzene-1,4-diyl, naphtalene-1,2-diyl, naphtalene-1,3-diyl, naphtalene-1,4-diyl. Benzenediyl (phenylene) is preferred, especially benzene-1,3-diyl.

5- to 10-membered heteroaryl represents for the purposes of the invention monovalent, 5- to 10-membered, heteroatom-containing aromatic radicals which may contain 1 to 4 heteroatoms which are preferably selected from O, S and N. Heteroaryl may be bonded via a ring carbon atom and ring heteroatom. The bonding preferably takes place via a ring carbon atom. Examples which may be mentioned are: fur-2-yl, fur-3-yl, thienyl, pyrrol-1-yl, pyrrol-2-yl, pyrrol-3-yl, imidazol-1-yl, imidazol-2-yl, pyrazolyl, thiazolyl, oxazolyl, pyrid-2-yl, pyrid-3-yl, pyrid-4-yl, pyrazinyl, pyrimidinyl, pyridazinyl, indolicenyl, indol-1-yl, indol-2-yl, indol-4-yl, indol-7-yl, benzo[b]thienyl, benzo[b]furyl, indazolyl, quinolyl, isoquinolyl, naphthyridinyl or quinazolinyl. Pyridyl and quinolyl are preferred.

5- to 6-membered heteroaryl represents for the purposes of the invention monovalent, 5- to 6-membered, heteroatom-containing aromatic radicals which may contain 1 to 4 heteroatoms which are preferably selected from O, S and N. The bonding preferably takes place via a ring carbon atom. Examples which may be mentioned are: fur-2-yl, fur-3-yl, thienyl, pyrrol-1-yl, pyrrol-2-yl, pyrrol-3-yl, imidazol-1-yl, imidazol-2-yl, pyrazolyl, thiazolyl, oxazolyl, pyrid-2-yl, pyrid-3-yl, pyrid-4-yl, pyrazinyl, pyrimidinyl, pyridazinyl. Pyridyl is preferred.

A saturated or partially unsaturated bridge comprising 3 to 7 bridge atoms which connects adjacent ring atoms in aryl and heteroaryl represents for the purposes of the invention a chain of hydrogen-saturated carbon atoms and/or heteroatoms which are preferably selected from O, S and N. The individual bridge atoms may be connected by single bonds or in some cases by multiple bonds, preferably double bonds. The ring atoms in aryl or heteroaryl which are connected together may be ortho, meta or peri relative to one another, and ortho which is preferred. Examples which may be mentioned are: propane-1,3-diyl, 1-aza-propane-1,3-diyl, 2-aza-propane-1,3-diyl, 1-thia-propane-1,3-diyl, 1-oxa-propane-1,3-diyl, butane-1,4-diyl, 1-aza-4-oxa-butane-1,4-diyl, 1,4-diaza-butane-1,4-diyl, but-2-ene-1,4-diyl, pentane-1,5-diyl, hexane-1,6-diyl, heptane-1,7-diyl. Examples of aryls or heteroaryls with bridges which may be mentioned are: indan-4-yl, inden-4-yl, indolin-5-yl, chroman-6-yl, chromen-6-yl, 1,2,3,4-tetrahydronaphthalen-5-yl, 5H-pyrido[2,3-d][1,2]oxazin-3-yl. The bridge is preferably saturated, and the bridge comprises 3 to 5 carbon atoms, it being possible for one of the bridge carbon atoms to be replaced by an oxygen, sulfur or nitrogen atom.

5- to 10-membered heteroarylene represents for the purposes of the invention divalent, 5- to 10-membered, heteroatom-containing aromatic radicals which may contain 1 to 4 heteroatoms which are preferably selected from O, S and N. Heteroarylene may be bonded via ring carbon atoms and/or ring heteroatoms. The bonding preferably takes place via ring carbon atoms. The two neighboring groups may be bonded ortho, meta or, if appropriate, para to the heteroarylene. Meta is preferred. Examples which may be mentioned are: furan-2,3-diyl, furan-3,4-diyl, thiophene-2,3-diyl, thiophene-2,4-diyl, thiophene-2,5-diyl, pyrrole-1,2-diyl, pyrrole-2,3-diyl, pyrrole-3,4-diyl, imidazole-diyl, pyrazole-diyl, pyridine-2,3-diyl, pyridine-2,4-diyl, pyridine-3,4-diyl, pyridine-3,5-diyl, pyridine-3,6-diyl, pyrazine-diyl, pyrimidine-diyl, pyridazine-diyl, indolicene-diyl, indole-1,2-diyl, indole-2,3-diyl, indole-4,5-diyl, indole-4,6-diyl, indol-4,7-diyl, benzo[b]thiophene-diyl, Benzo[b]furan-diyl, indazoline-diyl, quinoline-diyl, isoquinoline-diyl, naphthyridine-diyl or quinazoline-diyl. Pyridine-diyl and quinoline-diyl are preferred.

5- to 6-membered heteroarylene represents for the purposes of the invention divalent, 5- to 6-membered, heteroatom-containing aromatic radicals which may contain 1 to 4 heteroatoms which are preferably selected from O, S and N. Heteroarylene can be bonded via ring carbon atoms and/or ring heteroatoms. The bonding preferably takes place via ring carbon atoms. The two neighboring groups may be bonded ortho, meta or, where appropriate, para to the heteroarylene. Meta is preferred. Examples which may be mentioned are: furan-2,3-diyl, furan-3,4-diyl, thiophene-2,3-diyl, thiophene-2,4-diyl, thiophene-2,5-diyl, pyrrole-1,2-diyl, pyrrole-2,3-diyl, pyrrole-3,4-diyl, imidazole-diyl, pyrazole-diyl, pyridine-2,3-diyl, pyridine-2,4-diyl, pyridine-3,4-diyl, pyridine-3,5-diyl, pyridine-3,6-diyl, pyrazine-diyl, pyrimidine-diyl, pyridazine-diyl.

($C_1$–$C_8$)-Alkyl or ($C_1$–$C_6$)-alkyl represent for the purposes of the invention a straight-chain or branched alkyl radical with 1 to 8 or 6 carbon atoms. A straight-chain or branched alkyl radical with 1 to 6 carbon atoms is preferred. Examples which may be mentioned are: methyl, ethyl, n-propyl, isopropyl, t-butyl, n-pentyl and n-hexyl.

($C_4$–$C_6$)-Alkyl represents for the purposes of the invention a straight-chain or branched alkyl radical with 4 to 6 carbon atoms. Examples which may be mentioned are: n-butyl, i-pentyl, n-pentyl, hexyl, heptyl or octyl. Preference is given to n-butyl, n-pentyl and n-hexyl.

Partially fluorinated ($C_4$–$C_8$)-alkyl represents for the purposes of the invention a straight-chain or branched alkyl radical with 4 to 8 carbon atoms where some of the hydrogen atoms of the alkyl radical are replaced by fluorine atoms but the alkyl radical contains at least one hydrogen atom. Examples which may be mentioned are: 4,4,4-trifluorobut-1-yl, 4,4,4-trifluoro-3-trifluoromethyl-but-1-yl, 5,5,5-trifluoro-pent-1-yl, 4,4,5,5,5-pentafluoro-pent-1-yl. 4,4,4-Trifluorobut-1-yl is preferred.

($C_2$–$C_8$)-Alkenyl and ($C_2$–$C_6$)-alkenyl represent for the purposes of the invention a straight-chain or branched alkenyl radical with 2 to 8 or 6 carbon atoms and one or, where appropriate, more double bonds. A straight-chain or branched alkenyl radical with 2 to 4 carbon atoms is preferred. Examples which may be mentioned are: vinyl, allyl, isopropenyl and n-but-2-en-1-yl, n-hex-3-en-1-yl, oct-4-en-2-yl.

($C_4$–$C_6$)-Alkenyl represents for the purposes of the invention a straight-chain or branched alkenyl radical with 4 to 6 carbon atoms. Examples which may be mentioned are: n-but-2-en-1-yl, i-pentenyl, n-pentenyl, or hexenyl. Preference is given to n-but-2-en-1-yl, n-pent-2-en-1yl and n-hex-2-in-1-yl.

($C_2$–$C_8$)-Alkinyl or ($C_2$–$C_6$)-alkinyl represents for the purposes of the invention a straight-chain or branched alkinyl radical with 2 to 8 or 6 carbon atoms. A straight-chain or branched alkinyl radical with 2 to 4 carbon atoms is preferred. Examples which may be mentioned are: ethinyl, n-prop-2-in-1-yl and n-but-2-in-1-yl.

($C_4$–$C_6$)-Alkinyl represents for the purposes of the invention a straight-chain or branched alkinyl radical with 4 to 6 carbon atoms. Examples which may be mentioned are: n-but-2-in-1yl, i-pentinyl, n-pentinyl, or hexinyl. Preference is given to n-but-2-in-1-yl, n-pent-2-in-1yl and n-hex-2-in-1-yl.

($C_2$–$C_6$)-Alkanediyl represents for the purposes of the invention a straight-chain or branched alkanediyl radical with 2 to 6 carbon atoms. A straight-chain or branched alkanediyl radical with 2 to 4 carbon atoms is preferred. Examples which may be mentioned are: ethylene, propylene, propane-1,2-diyl, propane-2,2-diyl, butane-1,3-diyl, butane-2,4-diyl, pentane-2,4-diyl, 2-methyl-pentane-2,4-diyl.

($C_1$–$C_8$)-Alkoxy or ($C_1$–$C_6$)-alkoxy represent for the purposes of the invention a straight-chain or branched alkoxy radical with 1 to 8 or 6 carbon atoms. A straight-chain or branched alkoxy radical with 1 to 6 carbon atoms is preferred. Examples which may be mentioned are: methoxy, ethoxy, n-propoxy, isopropoxy, t-butoxy, n-pentoxy and n-hexoxy.

($C_1$–$C_8$)-Alkanoyl or ($C_1$–$C_6$)-alkanoyl represent for the purposes of the invention a straight-chain or branched alkanoyl radical with 1 to 8 or 6 carbon atoms. Examples which may be mentioned are: acetyl, propionyl, butyryl, isobutyryl, butylcarbonyl, isobutylcarbonyl, pentylcarbonyl and hexylcarbonyl or heptylcarbonyl. A straight-chain or branched alkanoyl radical with 1 to 4 carbon atoms is preferred. Acetyl and propionyl are particularly preferred.

($C_3$–$C_8$)-Cycloalkyl and ($C_3$–$C_6$)-cycloalkyl represent for the purposes of the invention a cycloalkyl group with 3 to 8 or 6 carbon atoms. Examples which may be mentioned are: cyclopropyl, cyclobutyl, cyclopentyl, cyclohexyl, cycloheptyl, cyclooctyl, Cyclopentyl and cyclohexyl are preferred.

Halogen includes for the purposes of the invention fluorine, chlorine, bromine and iodine. Chlorine or fluorine are preferred.

Tri-($C_1$–$C_6$)-alkylamines represent for the purposes of the invention tertiary amines where the amino nitrogen is substituted by three identical or different alkyl radicals. Examples which may be mentioned are: triethylamine, diisopropylethylamine, tri-n-propylamine.

Preference is given to compounds of the general formula (I)
in which
  A represents ($C_6$–$C_{10}$)-aryl or 5- to 10-membered heteroaryl,
    where aryl and heteroaryl are optionally substituted one or more times by radicals selected from the group of ($C_1$–$C_6$)-alkyl, ($C_2$–$C_6$)-alkenyl, ($C_2$–$C_6$)-alkinyl, ($C_1$–$C_6$)-alkoxy, ($C_1$–$C_6$)-alkanoyl, ($C_3$–$C_6$)-cycloalkyl, halogen, nitro, cyano, hydroxyl and trifluoromethoxy, where ($C_1$–$C_6$)-alkyl in turn is optionally substituted by halogen or hydroxyl,
  D represents phenylene or 5- to 6-membered heteroarylene, where phenylene and heteroarylene are optionally substituted one or more times by radicals selected from the group of ($C_1$–$C_6$)-alkyl, ($C_2$–$C_6$)-alkenyl, ($C_2$–$C_6$)-alkinyl, ($C_1$–$C_6$)-alkoxy, ($C_3$–$C_6$)-cycloalkyl, halogen, nitro, cyano, trifluoromethyl and trifluoromethoxy, and
  $R^1$ represents ($C_4$–$C_8$)-alkyl, or
    represents ($C_2$–$C_8$)-alkyl, where the carbon chain is interrupted by one or two heteroatoms selected from the group of —O— and —S— and
    where alkyl is optionally substituted one or more times by halogen,
  and the salts thereof,
with the exception of
  compounds of the general formula (I), in which D is phenylene and $R^1$ is 1,1,2,2,3,3,4,4,4-nonafluorobutyl, and
with the exception of
  [1,1'-biphenyl]-4-yl 1,1,2,2,3,3,4,4,5,5,6,6,7,7,8,8,8-heptadecafluoro-1-octanesulfonate and
  [1,1'-biphenyl]-2-yl 1,1,2,2,3,3,4,4,5,5,6,6,7,7,8,8,8-heptadecafluoro-1-octanesulfonate.

Preference is likewise given to compounds of the general formula (I)
in which
  A represents ($C_6$–$C_{10}$)-aryl or 5- to 10-membered heteroaryl,
    where adjacent ring atoms in aryl and heteroaryl are, where appropriate, connected by a saturated bridge comprising 3 to 5 bridge carbon atoms, and
    where aryl, heteroaryl and the bridge are optionally substituted one to three times by radicals selected from the group of ($C_1$–$C_6$)-alkyl, ($C_1$–$C_6$)-alkoxy, ($C_1$–$C_6$)-alkanoyl, halogen, nitro, cyano, hydroxyl, trifluoromethoxy, —$CONR^3R^4$, —$NR^7COR^8$, and —$NR^{11}R^{12}$, where ($C_1$–$C_6$)-alkyl in turn is optionally substituted by halogen, hydroxyl or —$NR^{13}R^4$,
    in which
    $R^3$, $R^4$, $R^7$, $R^8$, $R^{11}$, $R^{12}$, $R^{13}$ and $R^{14}$ are identical or different and denote hydrogen, optionally hydroxyl- or ($C_1$–$C_4$)-alkoxy-substituted ($C_1$–$C_6$)-alkyl or ($C_3$–$C_8$)-cycloalkyl,
  D represents phenylene or 6-membered heteroarylene, where phenylene and heteroarylene are optionally substituted once to three times by radicals from the group of ($C_1$–$C_4$)-alkyl, ($C_1$–$C_4$)-alkoxy, halogen, nitro, cyano, trifluoromethyl and trifluoromethoxy, and
  $R^1$ represents, where appropriate, partially fluorinated ($C_4$–$C_8$)-alkyl,
  and the salts thereof.

Particular preference is given to compounds of the general formula (I)
in which
  A represents phenyl, indanyl or 1,2,3,4-tetrahydronaphthyl,
    where the rings are optionally substituted one to three times by radicals selected from the group of ($C_1$–$C_4$)-alkyl, halogen, cyano, trifluoromethyl and trifluoromethoxy,
  D represents 1,3-phenylene, where the phenylene is optionally substituted up to twice by radicals selected from the group of ($C_1$–$C_4$)-alkyl, halogen, cyano, trifluoromethyl and trifluoromethoxy, and
  $R^1$ represents 4,4,4-trifluorobut-1-yl or n-pentyl,
  and the salts thereof.

A method for preparing compounds of the general formula (I) has additionally been found and is characterized in that

[A] a compound of the general formula (II)

$$A-D-OH \quad (II)$$

in which

A and D have the meaning indicated above, is reacted in an inert solvent in the presence of a suitable base with a compound of the general formula (III), $$X^1-SO_2-R^1 \quad (III)$$

in which $X^1$ represents a leaving group, and $R^1$ has the meaning indicated above, or,

[B] a compound of the general formula (IV)

$$A-X^2 \quad (IV)$$

in which

A has the meaning indicated above, and $X^2$ represents a radical selected from the group of —B(OR$^{16}$)$_2$, —SnR$^{17}$$_3$, —ZnR$^{18}$ and —SiR$^{19}$Cl$_2$, in which $R^{16}$ represents hydrogen or (C$_1$–C$_6$)-alkyl, or two $R^{16}$ radicals together denote (C$_2$–C$_6$)-alkanediyl or benzene-1,2-diyl, and $R^{17}$, $R^{18}$ and $R^{19}$ denote (C$_1$–C$_6$)-alkyl, is reacted in an inert solvent in the presence of a palladium catalyst and of a base with a compound of the general formula (V)

$$X^3-D-O-SO_2-R^1 \quad (V)$$

in which $X^3$ is a suitable leaving group, and

D and $R^1$ have the meaning indicated above, and, where appropriate, after [A] or [B] substituents in the reaction products are derivatized by conventional methods.

The methods according to the invention can be illustrated by way of example by the following formula diagrams:

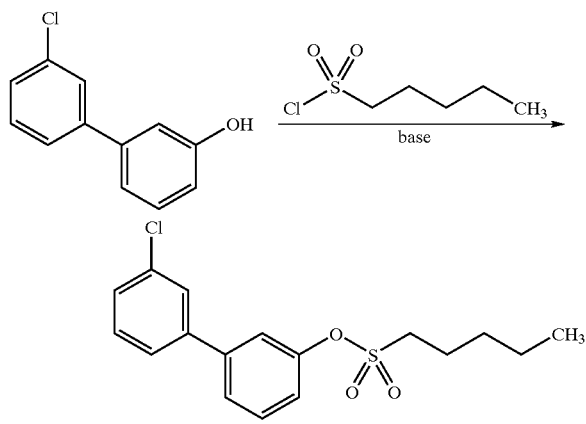
[A]

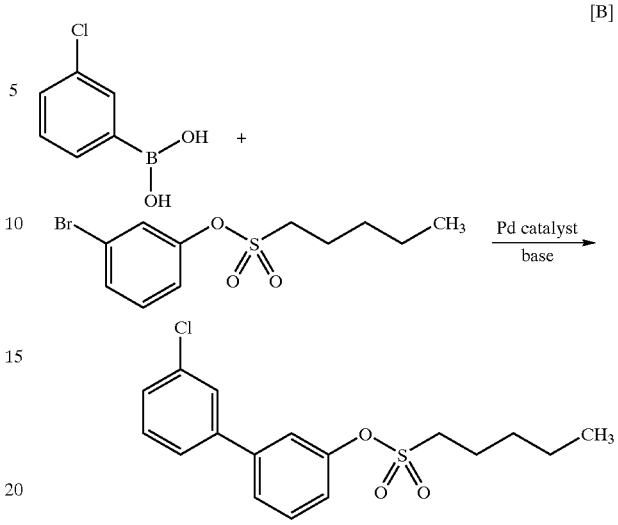
[B]

Inert solvents in the sense of the invention are solvents which are unchanged or changed only inconsiderably under the chosen reaction conditions.

Examples of inert solvents suitable for process [A] are ethers such as, for example, diethyl ether, glycol monomethyl or dimethyl ether, dioxane or tetrahydrofuran, or hydrocarbons such as benzene, p-cresol, toluene, xylene, cyclohexane or petroleum fractions or halogenated hydrocarbons such as methylene chloride, chloroform, tetrachloromethane, or dimethyl sulfoxide, dimethylformamide, hexamethylphosphoric triamide, ethyl acetate, pyridine, triethylamine or picoline. It is likewise possible to use mixtures of said solvents or two-phase systems with water. Methylene chloride, methylene chloride/water, tetrahydrofuran, dioxane and dioxane/water are particularly preferred.

Bases suitable for reaction [A] are organic amines, in particular tri(C$_1$–C$_6$)-alkylamines such as, for example, triethylamine or diisopropylethylamine, or heterocycles such as pyridine, methylpiperidine, piperidine or N-methylmorpholine, alkali metal or alkaline earth metal hydroxides or carbonates, such as, for example, sodium hydroxide, potassium hydroxide, sodium carbonate, potassium carbonate or alcohols such as, for example, sodium methanolate or sodium ethanolate. Triethyl-amine and sodium hydroxide are preferred.

The bases are generally employed in an amount of 0.1 mol to 5 mol, preferably of 1 mol to 3 mol, in each case based on 1 mol of the compounds of the general formula (II).

Process [A] can, where appropriate, also be carried out in the presence of a phase-transfer catalyst. Suitable phase-transfer catalyst examples are ammonium salts, preferably tetrabutylammonium bromide.

A suitable leaving group $X^1$ is, for example, a halogen, preferably a chlorine, or a sulfonato group, preferably triflate.

The reactions can be carried out under atmospheric pressure but also under elevated or reduced pressure (for example 0.5 to 3 bar). Atmospheric pressure is generally employed.

Process [A] is carried out at a temperature in the range from 0° C. to 100° C., preferably at 0° C. to 30° C. and under atmospheric pressure.

Process [B] represents a reductive coupling of the compounds of the general formulae (IV) and (V) as described, for example, in L. S. Hegedus, Organometallics in Synthesis, M. Schlosser, Ed., Wiley, 1994. Palladium-catalysed reductive couplings with boronic acids ("Suzuki coupling") are described, for example, in: *Tetrahedr. Lett.* 1985, 26, 2667–2670; *Chem. Commun.* 1984, 1287–1289; A. Suzuki and T. N. Mitchell in "Metal-catalyzed cross-coupling reactions", Ed. F. Diederich, P. J. Stang, Wiley-VCH, Weinheim 1998, pp. 49 et seq. and pp 167 et seq.

Examples of inert solvents which have proved suitable for reaction step [B] are the following: organic solvents such as ethers, such as, for example, diethyl ether, glycol monomethyl or dimethyl ether, dioxane or tetrahydrofuran, or hydrocarbons such as benzene, p-cresol, toluene, xylene, cyclohexane or petroleum fractions or halogenated hydrocarbons such as methylene chloride, chloroform, tetrachloromethane, or dimethyl sulfoxide, dimethylformamide, hexamethyl-phosphoric triamide, ethyl acetate, pyridine, triethylamine or picoline. It is likewise possible to use mixtures of said solvents, where appropriate also with water. Dimethoxyethane is particularly preferred.

Palladium catalysts which may be mentioned by way of example are Pd(II) compounds such as $Cl_2Pd(PPh_3)_2$ and $Pd(OAc)_2$, or Pd(0) compounds such as $Pd(PPh_3)_4$ and $Pd_2(dba)_3$.

Bases preferred for process [B] are alkali metal carbonates and bicarbonates, in particular sodium carbonate, alkali metal hydroxides, in particular sodium hydroxides, or organic amines, in particular tri($C_1$–$C_6$)-alkylamines such as, for example, triethylamine.

The leaving group $X^3$ can be, for example, halogen, preferably bromine or iodine, or a triflate.

The bases are generally employed in an amount of 0.1 mol to 5 mol, preferably of 1 mol to 3 mol, in each case based on 1 mol of the compounds of the general formula (IV).

The reactions can be carried out under atmospheric pressure but also under elevated or reduced pressure (for example 0.5 to 5 bar). Atmospheric pressure is generally employed.

The reactions are carried out at a temperature in the range from −20° C. to 120° C., preferably at 0° C. to 90° C.

Derivatizations of reaction products of reaction [A] or [B] take place by conventional methods and include reduction, oxidation, hydrolysis and/or condensation.

The compounds of the general formula (II) are known or can be prepared by generally known processes, for example by reacting a compound of the general formula (VI)

$$A\text{-}X^4 \qquad (VI)$$

in which
  A has the meaning indicated above, and
  $X^4$ has the meaning indicated for $X^3$ and is identical to or different from the latter,
with a compound of the general formula (VII)

$$X^5\text{-}D\text{-}O\text{—}R^{20} \qquad (VII)$$

in which
  $X^5$ has the meaning indicated for $X^2$ and is identical to or different from the latter,
  D has the meaning indicated above,
  $R^{20}$ represents a suitable hydroxyl protective group, preferably represents methyl, benzyl, allyl, methoxymethyl, 2-trimethylsilylethoxymethyl or trimethylsilyl,
under the conditions indicated for process [B], and subsequently eliminating the hydroxyl protective group under suitable conditions.

The introduction of hydroxyl protective groups and their elimination is known (for example T. W. Greene, P. G. M. Wuts, 'Protective Groups in Organic Synthesis', 2$^{nd}$ ed., New York, 1991 and the literature cited therein; *J.Org. Chem.* 1999, 64, 9719–9721).

Conversely, the compounds of the general formula (II) can also be prepared by coupling the compounds of the general formula (VIII)

$$A\text{-}X^6 \qquad (VIII)$$

in which
  A has the meaning indicated above, and
  $X^6$ has the meaning indicated for $X^2$ and is identical to or different from the latter,
with a compound of the general formula (IX)

$$X^7\text{-}D\text{-}O\text{—}R^{21} \qquad (IX)$$

in which
  $X^7$ has the meaning indicated for $X^3$ and is identical to or different from the latter,
  D has the meaning indicated above,
  $R^{21}$ has the meaning indicated for $R^{20}$ and is identical to or different from the latter,
under the conditions indicated for process [B].

In the case where A in compounds of the general formula (II) represents oxazole, thiazole or pyrazole, these can also be prepared by reacting a compound of the general formula (X)

$$H_2N\text{—}C(O)\text{-}D\text{-}O\text{—}R^{21} \qquad (X),$$

in which
  D and $R^{20}$ each have the meaning indicated above,
with a compound of the general formula (XI)

$$X^8\text{—}CH_2\text{—}C(O)\text{—}R^{22} \qquad (XI),$$

in which
  $X^8$ has the meaning indicated for $X^3$, and
  $R^{22}$ represents ($C_1$–$C_8$)-alkyl, ($C_2$–$C_8$)-alkenyl, ($C_2$–$C_8$)-alkinyl, trifluoromethyl or ($C_3$–$C_8$)-cycloalkyl,
to give a compound of the general formula (XII)

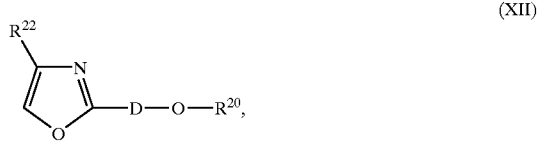

$$\text{(XII)}$$

in which
  D, $R^{20}$ and $R^{22}$ each have the meaning indicated above,
or
reacting a compound of the general formula (XIII)

$$X^9\text{—}CH_2\text{—}C(O)\text{-}D\text{-}O\text{—}R^{20} \qquad (XIII),$$

in which
  $X^9$ has the meaning indicated for $X^3$ and
  D and $R^{20}$ each have the meaning indicated above,
with a compound of the general formula (XIV)

$$R^{23}\text{—}C(S)\text{—}NH_2 \qquad (XIV),$$

in which

R[23] has the meaning indicated above for R[22], to give a compound of the general formula (XV)

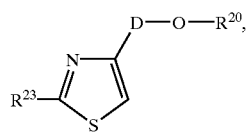  (XV)

in which

D, R[20] and R[23] each have the meaning indicated above, or reacting a compound of the general formula (XVI)

$R^{24}$—C(O)—CH$_2$—C(O)-D-O—R$^{20}$  (XVI), in which

D and R[20] each have the meaning indicated above, and R[24] has the meaning indicated above for R[22], with hydrazine, hydrazine hydrate or hydrazine salts to give a compound of the general formula (XVII)

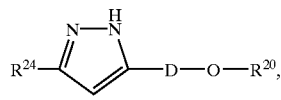  (XVII)

in which

D, R[20] and R[24] each have the meaning indicated above, and finally eliminating the hydroxyl protective group R[20] under suitable conditions in each of the compounds of the general formula (XII), (XV) or (XVII).

The compounds of the general formulae (X), (XI), (XIII), (XIV) and (XVI) are commercially available, known from the literature or can be prepared in analogy to processes known from the literature.

Compounds of the general formula (II) in which A and D are linked via a heteroatom such as, for example, a nitrogen atom, and a carbon atom, are known and can be obtained in analogy to processes known from the literature: for example Synthesis of 1-phenylpyrazole derivatives in K. Kirschke in *Methoden der Organischen Chemie* [*Methods of organic chemistry*] (*Houben-Weyl*) (E. Schaumann, Ed.) Thieme Verlag, Stuttgart 1994, pp399–763; Synthesis of 1-phenylpyrrole derivatives in *Heterocycles* 1996, 75–82 or *Chem. Pharm. Bull.* 1973, 21, 1516; Synthesis of 1-phenylimidazole derivatives in *J. Med. Chem.* 1989, 32, 575–583.

Compounds of the formula (III) are commercially available, are known from the literature or can be synthesized in analogy to processes known from the literature (compare, for example, *J. Chem. Soc. C* 1968, 1265; *Chem. Ber.* 1967, 100, 1696; fluorinated alkanesulfonyl chlorides can be obtained, for example, as described in WO-A-98/37061 or DE-A-19 422 64).

The compounds of the general formulae (VI) and (IX) are, when X[4] or X[7] represents iodine or bromine, commercially available, known from the literature or can be obtained by means of processes known from the literature (compare, for example, J. March, 'Advanced Organic Chemistry', 4th Ed., Wiley, 1992, pages 531–534 and the literature cited therein). When X[4] and X[7] represent triflate, the compounds of the general formulae (VI) and (IX) can be obtained from the corresponding alcohols in a known manner (concerning the use of triflates as leaving groups compare, for example, *Synth.* 1990,1145–1147). The corresponding alcohols are commercially available, known from the literature or can be obtained by means of processes known from the literature (for example concerning the synthesis of phenols compare, for example, J. March, 'Advanced Organic Chemistry', 4th Ed., Wiley, 1992, page 1295 and the literature cited therein).

The compounds of the general formulae (VII) and (VIII) are commercially available, known from the literature or can be synthesized in analogy to processes known from the literature (compare, for example, for aromatic boronic acids and boronic esters: *J. Chem. Soc. C* 1966, 566; *J. Org. Chem.* 1973, 38, 4016; *J. Org. Chem.* 1995, 60, 7508; *Tetrahedr. Lett.* 1997, 3447; or for tributyltin compounds: *Tetrahedr. Lett.* 1990, 31, 1347).

In a further aspect, the invention relates to compounds of the general formula (I)

in which

A represents ($C_6$–$C_{10}$)-aryl or heteroaryl with 5 to 10 ring atoms, where adjacent ring atoms in aryl and heteroaryl are, where appropriate, connected by a saturated or partially unsaturated bridge comprising 3 to 7 bridge atoms selected from the group of carbon, nitrogen, oxygen and sulfur, and where aryl, heteroaryl and the bridge are optionally substituted one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl, ($C_3$–$C_8$)-cycloalkyl, halogen, nitro, cyano, hydroxyl, trifluoromethoxy, —$CO_2R^2$, —$CONR^3R^4$, —$SO_2NR^5R^6$, —$NR^7COR^8$, —$NR^9SO_2R^{10}$ and —$NR^{11}R^{12}$, where ($C_1$–$C_8$)-alkyl in turn is optionally substituted by halogen, cyano, hydroxyl or —$NR^{13}R^{14}$, in which $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are identical or different and denote hydrogen, optionally hydroxyl- or ($C_1$–$C_4$)-alkoxy-substituted ($C_1$–$C_8$)-alkyl or ($C_3$–$C_8$)-cycloalkyl, D represents ($C_6$–$C_{10}$)-arylene or heteroarylene with 5 to 10 ring atoms, where arylene and heteroarylene are optionally substituted one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl, ($C_3$–$C_8$)-cycloalkyl, halogen, nitro, cyano, hydroxyl, trifluoromethyl, trifluoromethoxy and —$CO_2R^{15}$, in which $R^{15}$ denotes hydrogen, ($C_1$–$C_8$)-alkyl or ($C_3$–$C_8$)-cycloalkyl, and $R^1$ represents ($C_3$–$C_8$)-alkyl, represents ($C_2$–$C_8$)-alkyl where the carbon chain is interrupted by one or two heteroatoms or groups selected from the group of —O—, —S—, —SO— and —$SO_2$—, represents ($C_2$–$C_8$)-alkenyl, or represents ($C_2$–$C_8$)-alkinyl, where alkyl, alkenyl and alkinyl are optionally substituted one or more times by halogen and/or cyano, and the salts thereof, for the treatment and/or prophylaxis of diseases.

Preferred compounds of the general formula (I) for the treatment and/or prophylaxis of diseases are those where A represents ($C_6$–$C_{10}$)-aryl or 5- to 10-membered heteroaryl, where aryl and heteroaryl are optionally substituted one or more times by radicals selected from the group of $(C_1-C_6)$-alkyl, $(C_2-C_6)$-alkenyl, $(C_2-C_6)$-alkinyl, $(C_1-C_6)$-alkoxy, $(C_3-C_6)$-cycloalkyl, halogen, nitro, cyano, hydroxyl and trifluoromethoxy, where $(C_1-C_6)$-alkyl in turn is optionally substituted by halogen or hydroxyl, D represents phenylene or 5- to 6-membered heteroarylene, where phenylene and heteroarylene are optionally substituted one or more times by radicals selected from the group of $(C_1-C_6)$-alkyl, $(C_2-C_6)$-alkenyl, $(C_2-C_6)$-alkinyl, $(C_1-C_6)$-alkoxy, $(C_1-C_6)$-alkoxy, $(C_3-C_6)$-cycloalkyl, halogen, nitro, cyano, trifluoromethyl and trifluoromethoxy, and $R^1$ represents $(C_3-C_8)$-alkyl, or represents $(C_2-C_8)$-alkyl, where the carbon chain is interrupted by one or two heteroatoms selected from the group of —O— and —S— and where alkyl is optionally substituted one or more times by halogen.

Particularly preferred compounds of the general formula (I) are those in which D is a meta-substituted phenylene or 5- to 6-membered heteroarylene.

Likewise particularly preferred are compounds of the general formula (I) in which D is a phenylene or a 6-membered heteroarylene, where A and —O—SO$_2$—R$^1$ are in positions meta to one another on the phenylene or heteroarylene.

This can be illustrated by way of example by the following structural formula:

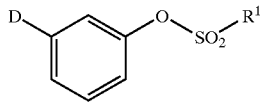

Compounds of the general formula (I) which are likewise particularly preferred are those in which $R^1$ represents $(C_4-C_6)$-alkyl, where the carbon chain is optionally interrupted by one or two heteroatoms or groups selected from the group of —O—,—S—,—SO— and —SO$_2$—, represents $(C_4-C_6)$-alkenyl, or represents $(C_4-C_6)$-alkinyl, where alkyl, alkenyl and alkinyl are optionally substituted one or more times by halogen and/or cyano, with the proviso that alkyl, alkenyl and alkinyl are not perfluorinated.

Very particularly preferred compounds of the general formula (I) are those in which $R^1$ denotes 4,4,4-trifluorobut-1-yl or n-pentyl.

Surprisingly, the compounds according to the invention show a valuable range of pharmacological actions which could not have been predicted.

They are distinguished by being highly effective agonists of the CB1 receptor and, in some cases, of the CB2 receptor. They can be employed alone or in combination with other medicaments for the prophylaxis and treatment of acute and/or chronic pain, and neurodegenerative disorders, in particular for the treatment of cancer-induced pain and chronic neuropathic pain like, for example, that associated with diabetic neuropathy, postherpetic neuralgia, peripheral nerve damage, central pain (as a consequence of cerebral ischemia) and trigeminal neuralgia, and other chronic pain such as, for example, lumbago, backache (lower back pain) or rheumatic pain.

The compounds according to the invention are likewise also suitable for the therapy of primary and/or secondary pathological states of the brain, for example during or after cerebral vasospasms, migraine, spasticity, hypoxia and/or anoxia whose origin has not previously been mentioned, perinatal asphyxia, autoimmune disease, metabolic and organic disorders which may be associated with damage to the brain, and damage to the brain as a consequence of primary brain disorders, for example epilepsy and atherosclerotic and/or arteriosclerotic changes. The compounds according to the invention are likewise suitable for the treatment of chronic or psychiatric disorders such as, for example, depression, neurodegenerative disorders such as, for example, Alzheimer's, Parkinson's or Huntington's disease, multiple sclerosis, amyotrophic lateral sclerosis (ALS), neurodegeneration due to acute and/or chronic viral or bacterial infections and multi-infarct dementia.

They can furthermore be employed in medicaments for the prophylaxis and treatment of emesis, nausea, glaucoma, asthma, anorexia, convulsions, rheumatism, sedation and movement disorders.

The substances according to the invention are also suitable for the treatment of disorders which are caused by bacterial and/or viral infections which are based on direct and/or indirect changes in the immune system or on dysregulation with involvement of the immune system, such as, for example, for local or systemic autoimmune diseases (for example lupus erythematosus in all its variants), inflammatory and/or autoimmunologically related disorders of the joints (for example rheumatoid arthritis, inflammations related to trauma), inflammatory and/or autoimmunologically related disorders of the skeletal and muscular systems, inflammatory and/or autoimmunologically related pathological processes of the internal organs (for example Crohn's disease, glomerulonephritis) and of the external organs (for example allergic reactions due to intake of airborne antigens) and of the central nervous system (for example multiple sclerosis, Alzheimer's disease, psychiatric disorders) and of the sensory organs, primary and/or secondary and/or autoimmunological disorders of the blood-forming system and of the immune system (for example rejection reactions, AIDS) itself, and for cutaneous disorders of inflammatory and/or immunological origin in humans and animals. These substances also act on the indirect symptoms of these disorders such as, for example, pain.

They are preferably used for the treatment of pain, spasticity, cerebral ischemias, craniocerebral trauma and Parkinson's disease.

The compounds according to the invention are additionally distinguished by high metabolic stability and high oral bioavailability. They are thus particularly suitable for oral therapy.

The in vitro action of the compounds according to the invention on cannabinoid receptors can be shown by the following bioassays:

1. Rats CB1 Luciferase Reporter Gene Test

Stock cultures of a rat CHOCB1 reporter cell line were prepared by the method described in WO-A-98/37061, page 55 et seq.

The following test protocol was used for the substance screening: the stock cultures were cultivated in 50% of Dulbecco's modified Eagle medium/50% F-12 (DMEM/F12) with 10% FCS at 37° C. under 10% CO$_2$ and split 1:10 after 2 to 3 days in each case. Test cultures were seeded at 5000cells per row in 96-well plates and cultured at 37° C. for 70 hours. The cultures were then cautiously washed with phosphate-buffered saline and reconstituted with serum-free Ultra-CHO medium (Bio-Whittaker). The substances dissolved in DMSO were diluted 1× in medium and pipetted into the test cultures (maximum DMSO final concentration in test mixture: 0.5%). 20 minutes later, forskolin was added and the cultures were then incubated in an incubator at 37° C. for 3 hours. The supernatants were then removed and the cells were lysed by adding 25 µl of lysis reagent (25 mM tris phosphate, pH 7.8 with 2 mM DTT, 10% glycerol, 3% Triton X100). Immediately thereafter luciferase substrate solution (2.5 mM ATP, 0.5 mM luciferin, 0.1 mM coenzyme A, 10 mM tricine, 1.35 mM $MgSO_4$, 15 mM DTT, pH 7.8) and briefly shaken, and the luciferase activity was measured using a Hamamatsu camera system.

To inactivate $G_i$ proteins, the test cultures were treated with 5 ng/ml (final concentration) pertussis toxin for 16 hours before the test.

The $IC_{50}$ values were calculated using the GraphPadPrism program (Hill equation, specifically: one-site competition).

Examples 3 and 17 show $IC_{50}$ values of 2.4 nM and 16 nM, respectively, in this test.

2. hCB2 Luciferase Reporter Gene Test

CHOluc9 cells were stably transfected with the human CB2 receptor. Transfection, clone selection and test development were carried out in analogy to the work on the rat CB1 receptor. The following test protocol was used for pharmacological characterization of the cells and for substance testing:

The stock cultures were cultivated in 50% of Dulbecco's modified Eagle medium/50% F-12 (DMEM/F12) with 10% FCS at 37° C. under 10% $CO_2$ and split 1:10 after 2 to 3 days in each case. Test cultures were seeded at 5000 cells per row in 96-well plates in DMEM/F12 medium with 5% FCS and cultured at 37° C. for 70 hours. The cultures were then removed from the medium and reconstituted with serum-free Ultra-CHO medium (Bio-Whittaker). The substances dissolved in DMSO (200× final concentration) were pipetted into the test cultures (maximum DMSO final concentration in test mixture: 0.5%). 20 minutes later, forskolin was added and the cultures were then incubated in an incubator at 37° C. for 3.5 hours. The supernatants were then removed and the cells were lysed by adding 25 µl of lysis reagent (25 mM tris phosphate, pH 7.8 with 2 mM DTT, 10% glycerol, 3% Triton X100). Immediately thereafter 50 µl of luciferase substrate solution, doubly concentrated, (5 mM ATP, 1 mM luciferin, 0.2 mM coenzyme A, 10 mM tricine, 1.35 mM $MgSO_4$, 15 mM DTT, pH 7.8) were added and briefly shaken, and the luciferase activity was determined using a photomultiplier camera measuring system (Hamamatsu).

The $IC_{50}$ values were calculated using the GraphPad Prism™ program (Hill equation; specifically one-site competition).

3. Binding to Rat Cortex Membranes

Membrane protein is prepared from various tissues and from cells by standard methods. Buffer, labeled ligand, DMSO or test substance are pipetted together, then 100 µg of protein are added, and the mixture is thoroughly mixed and incubated in a waterbath at 30° C. for 60 min. After completion of the incubation time, the reaction is stopped by adding ice-cooled incubation buffer to each tube. Filtration is followed by washing with ¾ ml of incubation buffer. The filters are transferred into minivials, and the radioactivity is determined in a liquid scintillation counter.

The metabolic stability of the compounds according to the invention can be found in the following in vitro assay:

4. Microsomal Stability Investigation

The metabolic stability of the compounds according to the invention can be measured in rat liver microsomes (in analogy to *J. Pharmacol. Exp. Ther.* 1997, 283. 46–58).

To determine the microsomal stability and extrapolate to the maximum possible bioavailability (Fmax) owing to the first-past effect in the liver (phase 1 reactions), the substance is incubated in low concentration with microsomal protein, with addition of cofactors, at 37° C. for 15 minutes.

The incubation and the sampling take place on a modified automatic pipettor from Canberra Packard.

The bioavailability of the compounds according to the invention, and other pharmacokinetic parameters, can be determined in vivo in the following way:

5. Pharmacokinetics in the Rat a) Intravenous Infusion

The substance is infused through a Braunüle in a lateral tail vein directly into the blood stream over 15 minutes. A calibrated 20 ml syringe is used for accurate administration of the chosen dose and volume. A Braun Melsungen No. 152440/1 pump is used for the infusion.

b) Oral Administration

The substance is administered as bolus by gavage.

c) Sampling and Workup

Blood and Plasma

Blood samples are collected from catheterized animals jugular vein) in heparinized tubes. The blood is centrifuged and the plasma is prepared in a suitable manner for analysis (LC-MS-MS). The plasma is stored at <−15° C. until analyzed.

d) Pharmacokinetic Results of Example 2

Microsomal data (rat liver microsomes) predict a maximum possible availability of up to 100%.

The pharmacokinetic parameters derived from the in vivo experiments (rat) are:

Oral Data: (dose: 3 mg/kg): $AUC_{norm}$: 0.322 kg*h/l, $C_{max,norm}$: 0.0674 kg/l, $t_{max}$: 3 h, $t_{1/2}$: 1.7 h, F: 100%.

I.V. Data: (dose: 0.3 mg/kg): CL: 3.1 l/h/kg, $V_{ss}$: 5.8 l/kg, $t_{1/2}$: 2.2 h.

The in vivo effect of the compounds according to the invention can be shown, for example, in the following animal models:

6. Hypothermia (Rat)

The in vivo agonistic effect on the CB1 receptor was examined in the rat hypothermia assay.

Five minutes after determining the basal body temperature via an esophageal temperature probe, the test substance is administered (orally). A control group receives, likewise orally, only the solvent for the test substances (Cremophors EL 1–10%+distilled water). The body temperature is measured 120 and 240 minutes after oral administration. The size of the group for each dose is 5–7 animals (rats).

Rat Hypothermia Agonism Test

| Example | $ED_{-1° C.}$[a] [mg/kg] |
|---------|--------------------------|
| 2       | 5 mg/kg                  |

[a] Effective dose for reducing the body temperature by 1° C.

The suitability of the compounds according to the invention for the treatment of states of pain can be shown in the following animal models:

7. Axotomy of Sciatic Branches in the Rat (Chronic Pain Model)

Under pentobarbital anesthesia, the trifurcation of a sciatic nerve is exposed, and the peroneal and tibial branches are axotomized after the nerves have been ligated proximal of the axotomy site. Control animals undergo a sham operation. After the operation, the axotomized animals develop chronic mechanical allodynia and thermal hyperalgesia.

The mechanical allodynia is tested, comparing with sham-operated animals, with the aid of a pressure transducer (electronic von Frey anesthesiometer, IITC Inc.-Life Science Instruments, Woodland Hills, Calif., USA).

The thermal hyperalgesia can be determined by measuring the latency time within which a rat removes a paw from the area of a radiant heat source (plantar test, Ugo Basile (Milan)).

The substance was administered by various administration routes (i.v., i.p., orally, i.t., i.c.v., transdermally) at various times before the pain testing.

Example 2 reduces the hyperalgesia in the model at a minimally effective dose of 1 mg/kg orally (acute administration, 60 minutes before the test).

The suitability of the compounds according to the invention for example for the treatment of neurodegenerative disorders can be shown in the model of permanent focal cerebral ischemia in the rat (MCA-O) or in the model of subdural hematoma in the rat (SDH) (WO-A-98/37061, page 60 et seq.).

8.6-Hydroxydopamine (6-OH-DA) Lesion in the Rat

Degeneration of dopaminergic nigrostriatal and striatopallidal neurotransmission is the main characteristic of Parkinson's disease. The clinical picture of Parkinson's disease can be simulated to a large extent in an animal model in which the neurotoxin 6-OH-DA is injected intracerebrally in rats.

Male rats (Harlan Winkelmann, Germany; weight at start of test: 200–250 g) were used for the experiments described. The experimental animals were housed under controlled conditions (humidity, temperature) with a 12-hour light/dark cycle. Those animals not involved in an experiment had free access to water and feed.

On the day of the operation, 30 minutes before the lesion, pargyline (Sigma, St. Louis, Mo., USA; 50 mg/kg i.p.) and desmethylimipramine HCl (Sigma; 25 mg/kg i.p.) were administered to the animals in order respectively to suppress 6-hydroxydopamine metabolism and prevent uptake of 6-hydroxydopamine in noradrenergic structures. After induction of anesthesia by sodium pentobarbital (50 mg/kg i.p.), the experimental animals were fixed in a stereotactic frame. The nigrostriatal neurotransmission lesion was produced by a unilateral single injection of 8 $\mu$g of 6-OH-DA HBr (Sigma, St. Louis, Mo., USA), dissolved in 4 $\mu$l of a 0.01% strength ascorbic acid/saline solution. The solution was injected slowly at 1 $\mu$l/min. The König and Klippel injection coordinates are: 2.4 mm anterior, 1.49 mm lateral, –2.7 mm ventral. After the injection, the hypodermic needle was left in situ for 5 minutes in order to facilitate diffusion of the neurotoxin.

After the operation, the animals were placed on a warm plate and, after regaining consciousness while being monitored, returned to their cage and received feed and water ad libitum.

In the active substance group, the animals were treated with the substance from one day after the operation until the end of the experiment 28 days after the operation.

The motor deficits after the lesion were quantified using the following test as described in the respective literature:

a) Staircase Test (Forepaw Coordination Test)

Barnéoud et al: Effects of complete and partial lesions of the dopaminergic mesotelencephalic system on skilled forelimb use in the rat. *Neuroscience* 1995, 67, 837–848.

b) Accelerating Rotarod Test (Test of Balance):

Spooren et al.: Effects of the prototypical mGlu$_5$ receptor antagonist 2-methyl-6-(phenylethynyl)-pyridine on rotarod, locomotor activity and rotational responses in unilateral 6-OHDA-lesioned rats. *Eur. J. Pharmacol.* 2000, 406, 403–410.

c) Measurement of the Pulling Force of the Forepaws:

Dunnet et al.: A lateralised grip strength test to evaluate unilateral nigrostriatal lesions in rats. *Neurosci. Lett.* 1998, 246, 1–4.

For example, there is an improvement in the fine coordination of the forepaws in the staircase test after an oral dose of 1.0 mg/kg of Example 2 bid.

The novel active substances can be converted in a known manner into conventional formulations such as tablets, coated tablets, pills, granules, aerosols, syrups, emulsions, suspensions and solutions by use of inert, nontoxic, pharmaceutically suitable carriers or solvents. In these the therapeutically active compound should be present in each case in a concentration of about 0.5 to 90% by weight of the complete mixture, that is to say in amounts which are sufficient to achieve the stated dose range.

The formulations are produced for example by extending the active substances with solvents and/or carriers, where appropriate with use of emulsifiers and/or dispersants, it being possible to use, for example in the case where water is used as diluent, where appropriate organic solvents as auxiliary solvents.

Administration takes place in a conventional way, preferably orally, transdermally or parenterally, in particular perlingually or or intravenously. However, it can also take place by inhalation through the mouth or nose, for example with the aid of sprays, or topically through the skin.

In general, it has proved advantageous to administer amounts of about 0.001 to 10 mg/kg on oral administration, preferably about 0.005 to 3 mg/kg of body weight, to achieve effective results.

It may nevertheless be necessary where appropriate to deviate from the stated amounts, in particular depending on the body weight and the mode of administration, on the individual response to the medicament, the nature of its formulation and the time or interval over which administration takes place. Thus, in some cases it may be sufficient to make do with less than the aforementioned minimum amount, whereas in other cases the upper limit mentioned must be exceeded. In the case of administration of larger amounts, it may be advisable to distribute these in several individual doses over the day.

The determination of the retention time of starting compounds and preparation examples by HPLC took place under the following conditions:

Column: Kromasil C18 60*2; volume injected 1.00 $\mu$l; flow rate: 0.75 ml/min; eluent: A=0.01M aq H$_3$PO$_4$, B=CH$_3$CN; gradient [t(min): A/B)]: 0: 90/10; 0.5: 90/10, 4.5: 10/90; 6.5: 10/90; 7.5: 90/10.

Starting Compounds

EXAMPLE 1A 3-(3-Chlorophenyl)phenol a) 3-(3-Chlorophenyl)phenyl methyl ether

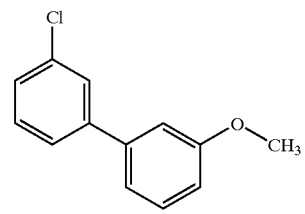

Under argon, 1.42 ml of 2M sodium carbonate solution, 12.5 mg of dichlorobis-(triphenylphosphine)palladium(II) and 236 mg (1.550 mmol) of 3-methoxyphenylboronic acid (*J. Chem. Soc. Perkin I* 1996, 2591–97) are added to 250 mg (1.293 mmol) of 3-bromochlorobenzene in 2.5 ml of dimethoxyethane, and the mixture is stirred under reflux for 18 hours. After cooling, the reaction mixture is filtered through a cartridge packed with 3 g of Extrelut® NT3 (Merck), and the product is washed out with dichloromethane. The solvent is distilled off under reduced pressure. The residue is purified by chromatography on silica gel (0.04–0.063 mm) with cyclohexane/dichloromethane 6/1 as mobile phase.

Yield: 261 mg (92.5% of theory) $R_f$ (cyclohexane/dichloromethane 6/1)=0.36 MS (EI): 219 (M+H) HPLC, retention time=5.28 min b) 3-(3-Chlorophenyl)phenol

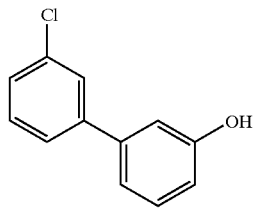

220 mg (1.01 mmol) of 3-(3-chlorophenyl)phenyl methyl ether from Example 1 Aa are dissolved in 2 ml of glacial acetic acid and, after addition of 1.3 ml of 48 per cent strength aqueous hydrobromic acid, stirred at the reflux temperature for 4 h. The reaction mixture is evaporated to dryness under reduced pressure, the residue is mixed with 1.5 ml of water and 10 ml of dichloromethane and added to a cartridge packed with 3 g of Extrelut® NT3 (Merck), and the product is washed out with dichloromethane. The solvent is distilled off under reduced pressure, and the residue is purified by chromatography on silica gel (0.04–0.063 mm) with cyclohexane/dichloromethane 10/1 as mobile phase.

Yield: 204 mg (98% of theory) $R_f$ (cyclohexane/dichloromethane 10/1)=0.24 MS (EI): 205 (M+H) HPLC, retention time=4.43 min The compounds in Table 1A were obtained by the process described for Example 1A from the appropriate compounds of the general formula (VI) with the appropriate compounds of the general formula (VII), namely 3-methoxyphenylboronic acid (3-MPB) or 4-methoxyphenylboronic acid (4-MPB; *Tetrahedron* 1992, 48, 8073–8078).

TABLE 1A

| Example | Structure | $X^4$ [starting compound (VI)] | Starting compound (VII) | Yield [%] | HPLC ($t_{ret}$) [min] | MS (EI) [m/z] |
|---|---|---|---|---|---|---|
| 2A | 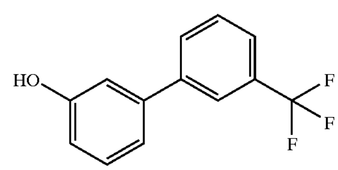 | Br[1)] | 3-MPB | 89.2 | 4.67 | 239 (M + H) |
| 3A | 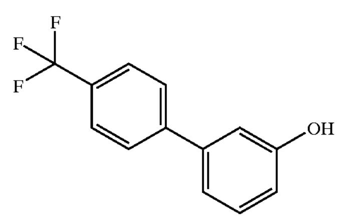 | Br | 3-MPB | 93.18 | 4.55 | 239 (M + H) |
| 4A | 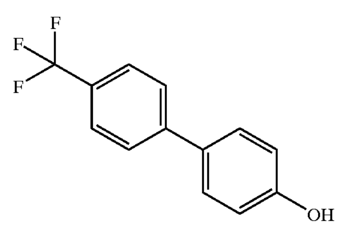 | Br | 4-MPB | 85.33 | 4.55 | 239 (M + H) |
| 5A | 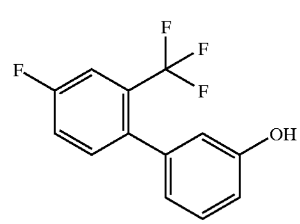 | Br | 3-MPB | 44.15 | 4.5 | 257 (M + H) |

TABLE 1A-continued

| Example | Structure | X⁴ [starting compound (VI)] | Starting compound (VII) | Yield [%] | HPLC ($t_{ret}$) [min] | MS (EI) [m/z] |
|---|---|---|---|---|---|---|
| 6A | 2-(trifluoromethyl)phenyl-3-hydroxyphenyl | Br | 3-MPB | 93.35 | 4.41 | 239 (M + H) |
| 7A | 2-(trifluoromethyl)phenyl-4-hydroxyphenyl | Br | 4-MPB | 91.29 | 4.41 | 239 (M + H) |
| 8A | 3-(trifluoromethoxy)phenyl-3-hydroxyphenyl | Br | 3-MPB | 94 | 4.6 | 255 (M + H) |
| 9A | 3-(trifluoromethoxy)phenyl-4-hydroxyphenyl | Br | 4-MPB | 86.24 | 4.6 | 255 (M + H) |
| 10A | 3-chlorophenyl-3-hydroxyphenyl | Br | 3-MPB | 98.06 | 4.43 | 205 (M + H) |
| 11A | 4-methyl-2-(3-hydroxyphenyl)pyridine | Br | 3-MPB | 50.3 | 0.71 | 186 (M + H) |

TABLE 1A-continued

| Example | Structure | X⁴ [starting compound (VI)] | Starting compound (VII) | Yield [%] | HPLC (t_ret) [min] | MS (EI) [m/z] |
|---|---|---|---|---|---|---|
| 12A | (3-trifluoromethylbiphenyl-4-ol) | Br | 4-MPB | 94.19 | 4.51 | 239 (M + H) |
| 13A | (3'-ethyl-biphenyl-3-ol) | Br | 3-MPB | 81.54 | 4.55 | 199 (M + H) |
| 14A | (3-(3-trifluoromethyl-pyridin-2-yl)phenol) | Br | 3-MPB | 61.79 | 3.67 | 240 (M + H) |
| 15A | (2',5'-dichloro-biphenyl-3-ol) | Br | 3-MPB | 95.61 | 4.6 | 240 (M + H) |
| 16A | (2'-dimethylaminomethyl-biphenyl-3-ol) | Br | 3-MPB | 54.43 | 2.52 | 228 (M + H) |
| 17A | (2',3'-dichloro-biphenyl-3-ol) | Br | 3-MPB | 97.23 | 4.54 | 240 (M + H) |
| 18A | (2'-(1-hydroxyethyl)-biphenyl-3-ol) | Br | 3-MPB | 61.84 | 3.62 | 215 (M + H) |

TABLE 1A-continued

| Example | Structure | X⁴ [starting compound (VI)] | Starting compound (VII) | Yield [%] | HPLC ($t_{ret}$) [min] | MS (EI) [m/z] |
|---|---|---|---|---|---|---|
| 19A | 3-nitro-3'-hydroxybiphenyl | Br | 3-MPB | 91.59 | 4.11 | 216 (M + H) |
| 20A | 3-acetyl-3'-hydroxybiphenyl | Br | 3-MPB | 92.74 | 3.85 | 213 (M + H) |
| 21A | 3,5-dichloro-3'-hydroxybiphenyl | Br | 3-MPB | 89.6 | 4.78 | 240 (M + H) |
| 23A | 2-isopropyl-3'-hydroxybiphenyl | Br | 3-MPB | 95.14 | 4.65 | 213 (M + H) |
| 24A | 8-(3-hydroxyphenyl)quinoline | Br | 3-MPB | 82.91 | 3.38 | 222 (M + H) |
| 25A | 4-(3-hydroxyphenyl)-3-methylbenzisoxazole | OTf²⁾ | 3-MPB | 78.97 | 4.05 | 226 (M + H) |

TABLE 1A-continued

| Example | Structure | X⁴ [starting compound (VI)] | Starting compound (VII) | Yield [%] | HPLC ($t_{ret}$) [min] | MS (EI) [m/z] |
|---|---|---|---|---|---|---|
| 26A | (1-methyl-1H-indazol-4-yl)-3-hydroxyphenyl | Br³⁾ | 3-MPB | 85.13 | 3.81 | (DCI, NH₃) 225 (M + H) |
| 27A | 2-methyl-3-nitrobiphenyl-3'-ol | Br | 3-MPB | 77.55 | 4.24 | (DCI, NH₃) 247 (M + NH₄) |
| 28A | 3'-hydroxybiphenyl-2-carboxamide | Br | 3-MPB | 89.03 | 3.43 | (DCI, NH₃) 231(M + NH₄) |
| 29A | 2-methyl-4-(3-hydroxyphenyl)benzoxazole | OTf | 3-MPB | 46.96 | 3.01 | DCI/NH₃: 226 (M + H) |
| 30A | 2,2-difluoro-4-(3-hydroxyphenyl)-1,3-benzodioxole | OTf | 3-MPB | 51.31 | 4.49 | 250 (M) |
| 31A | 7-(3-hydroxyphenyl)benzofuran | OTf | 3-MPB | 47.69 | 4.86 | DCI/NH₃: 242 (M + NH₄) |
| 32A | 3'-(hydroxymethyl)biphenyl-3-ol | OTf | 3-MPB | 41.28 | 3.42 | 200 (M) |

TABLE 1A-continued

| Example | Structure | X⁴ [starting compound (VI)] | Starting compound (VII) | Yield [%] | HPLC ($t_{ret}$) [min] | MS (EI) [m/z] |
|---|---|---|---|---|---|---|
| 33A | 3-chloro-2-nitro-phenyl-(3-hydroxyphenyl) | OTf | 3-MPB | 87.14 | 4.43 | 249 (M) |
| 34A | 3-(dimethylamino)phenyl-(3-hydroxyphenyl) | OTf | 3-MPB | 83.82 | 2.77 | 213 (M) |
| 35A | 5-isoquinolinyl-(3-hydroxyphenyl) | OTf | 3-MPB | 90.77 | 2.61 | 221 (M) |
| 36A | 4-indanyl-(3-hydroxyphenyl) | OTf | 3-MPB | 92.09 | 4.75 | 210 (M) |
| 37A | 5,6,7,8-tetrahydronaphthalen-1-yl-(3-hydroxyphenyl) | OTf | 3-MPB | 98.1 | 4.89 | 224 (M) |

TABLE 1A-continued

| Example | Structure | X⁴ [starting compound (VI)] | Starting compound (VII) | Yield [%] | HPLC (t$_{ret}$) [min] | MS (EI) [m/z] |
|---|---|---|---|---|---|---|
| 38A | 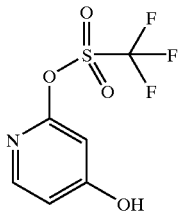 | Br | 3-MPB | 96.46 | 4.61 | 198 (M) |

[1)] J.Amer.Chem.Soc. 1943, 65, 389
[2)] Prepared from 3-methyl-1,2-benzisoxazol-4-ol (J. Chem. Soc. Perkin I 1973, 2220–2222)
[3)] Prepared by N-methylation of 4-bromo-1H-indazole (J. Heterocycl. Chem. 1984, 21, 1063) with methyl iodide and potassium carbonate in DMF

EXAMPLE 39A

4-Hydroxy-2-pyridinyl trifluoromethanesulfonate

Under argon, 5.91 g (53.2 mmol) of dihydroxypyridine are suspended in 54.2 ml of pyridine and cooled to 0° C. To this are added dropwise, over the course of about 10 minutes, 8.55 ml (50.5 mmol) of trifluoromethanesulfonic anhydride. The mixture is then allowed to reach room temperature and is stirred for 30 minutes. Working up takes place by adding water, extracting with ethyl acetate, washing, drying and evaporating in a rotary evaporator. The residue is purified by chromatography on 200 g of silica gel (0.04–0.063 mm) with cyclohexane/ethyl acetate (9:1 to 1:1).

Yield: 3.47 g (26.8% of theory)

EXAMPLE 40A

2-Trifluoromethylsulfonyloxy-4-pyridinyl 4,4,4-trifluoro-1-butanesulfonate

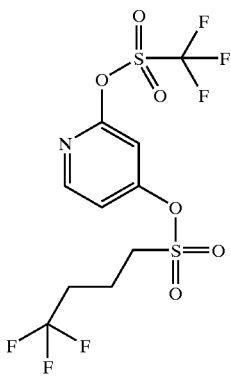

Under argon, 550 mg (2.26 mmol) of 4-hydroxy-2-pyridinyl trifluoromethanesulfonate (Example 39A) are suspended in 15 ml of dichloromethane at room temperature. 2 ml of a 40% strength solution of tetrabutylammonium hydroxide in water are added dropwise to this. Then 476 mg (2.26 mmol) of 4,4,4-trifluoro-1-butanesulfonyl chloride are added and allowed to react for 20 minutes. Working up takes place by adding water, extracting with ethyl acetate, washing, drying and evaporating in a rotary evaporator. The residue is purified by chromatography on 20 g of silica gel (0.04–0.063 mm) with cyclohexane/ethyl acetate 2:1 to 1:1).

Yield: 590 mg (62.5% of theory)

EXAMPLE 41A

Methyl 3-(4-ethyl-1,3-oxazol-2-yl)phenyl ether

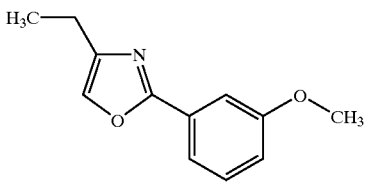

A suspension of 1.81 g (12.0 mmol) of 3-methoxybenzamide and 1.81 g (12.0 mmol) of 1-bromo-2-butanone in 11 ml of toluene is stirred under reflux for 24 hours. 70 ml of dichloromethane are added, and the mixture is washed with NaHCO$_3$ (5% strength aqueous solution) until the pH is adjusted to 9. After phase separation, drying of the organic phase with Na$_2$SO$_4$, and filtration, the solvent is distilled off under reduced pressure. The residue is purified by chromatography on silica gel (0.04–0.063 mm) with cyclohexane/ethyl acetate 6:1 as mobile phase.

Yield: 900.9 mg (32.7% of theory) R$_f$ (cyclohexane/ethyl acetate 3:1)=0.55 MS (DCI): 204 (M+H) HPLC, retention time=4.34 min $^1$H-NMR (300 MHz, DMSO-d$_6$): δ=1.20 (t, 3 H), 2.55 (m, 2 H), 3.78 (s, 3 H), 7.08 (ddd, 1 H), 7.40–7.58 (m, 3 H), 7.92 (s, 1 H).

EXAMPLE 42A

Methyl 3-(4-trifluoromethyl-1,3-oxazol-2-yl)phenyl ether

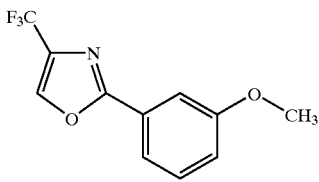

a) A suspension of 1.81 g (12.0 mmol) of 3-methoxybenzamide and 1.76 g (12.0 mmol) of 1-chloro-3,3,3-trifluoroacetone in 11 ml of toluene is stirred under reflux for 24 hours. 70 ml of dichloromethane are added, and the mixture is washed with NaHCO$_3$ (5% strength aqueous solution) until the pH is adjusted to 9. Phase separation is followed by washing with saturated aqueous NaCl solution and drying of the organic phase over Na$_2$SO$_4$. The residue obtained after filtering and distilling off the solvent under reduced pressure is purified by chromatography on silica gel (0.04–0.063 mm) with cyclohexane/ethyl acetate 6:1 as mobile phase. This results in a 79.5% yield of 3-methoxy-N-(3,3,3-trifluoro-2-oxopropyl)benzamide as uncyclized product.

b) 1.72 g (6.57 mmol) of 3-methoxy-N-(3,3,3-trifluoro-2-oxopropyl)benzamide from stage a) are stirred in 15 ml of phosphorus oxychloride under reflux for 4 h. After dilution with 20 ml of ethyl acetate, the solvent is cautiously added to 5 ml of ice-water. The organic phase is extracted three times with 20 ml of ethyl acetate each time and the combined organic phases are dried over Na$_2$SO$_4$. The solvent is distilled off under reduced pressure, and the residue is purified by chromatography on silica gel (0.04–0.063 mm) with cyclohexane/ethyl acetate 6:1 as mobile phase.

Yield: 1.20 g (53.9% of theory) R$_f$ (cyclohexane/ethyl acetate 3:1)=0.70 MS (DCI): 244 (M+H) HPLC, retention time=4.73 min $^1$H-NMR (300 MHz, DMSO-d$_6$): δ=3.86 (s, 3 H), 7.19 (ddd, 1 H), 7.40–7.66 (m, 3 H), 9.04 (m, 1 H).

EXAMPLE 43A

Methyl 3-(2-methyl-1,3-thiazol-4-yl)phenyl ether

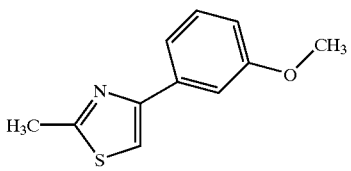

A suspension of 1.17 g (15.6 mmol) of thioacetamide and 2.75 g (12.0 mmol) of 3-methoxy-bromoacetophenone in 40 ml of toluene is stirred under reflux for 24 hours. 100 ml of ethyl acetate and 15 ml of water are added. Phase separation is followed by extraction three times with 30 ml of ethyl acetate each time and drying of the combined organic phases over Na$_2$SO$_4$. After filtration, the solvent is distilled off under reduced pressure and the residue is purified by chromatograpy on silica gel (0.04–0.063 mm) with cyclohexane/ethyl acetate 7:1 as mobile phase.

Yield: 2.63 g (98.5% of theory) R$_f$(cyclohexane/ethyl acetate 5:1)=0.49 MS (DCI): 206 (M+H) HPLC, retention time=4.23 min $^1$H-NMR (300 MHz, MeOH-d$_4$): δ=2.75 (s, 3 H), 3.84 (s, 3 H), 6.89 (ddd, 1 H), 7.31 (dd, 1 H), 7.40–7.46 (m, 2 H), 7.61 (s, 1 H).

EXAMPLE 44A

Methyl 3-[3-(trifluoromethyl)-1H-pyrazol-5-yl]phenyl ether

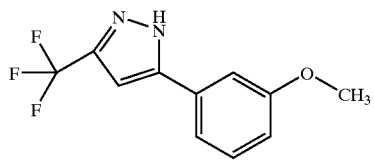

A solution of 500 mg (2.03 mmol) of 4,4,4-trifluoro-1-(3-methoxyphenyl)-butane-1,3-dione and 156.2 mg (2.23 mmol) of hydrazine monohydrochloride in 35 ml of ethanol is stirred under reflux for 24 hours. The ethanol is distilled off under reduced pressure, and the resulting residue is taken up in 20 ml of ethyl acetate. It is washed twice with water and once with saturated aqueous NaCl solution. After drying of the organic phase over Na$_2$SO$_4$ and filtration, the solvent is distilled off under reduced pressure.

Yield: 474.7 mg (85.2% of theory) R$_f$(cyclohexane/ethyl acetate 3:1)=0.27 MS (DCI): 243 (M+H), 260 (M+NH4) HPLC, retention time=4.40 min $^1$H-NMR (300 MHz, DMSO-d$_6$): δ=3.82 (s, 3 H), 6.98 (m, 1 H), 7.25 (s, 1 H), 7.36–7.47 (m, 3 H), 14.07 (br. s, 1 H).

EXAMPLE 45A 3-(4-Ethyl-1,3-oxazol-2-yl)phenol

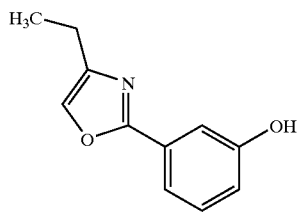

Under argon, 9.47 ml of boron tribromide (1.0 M in CH$_2$Cl$_2$) are added dropwise at 0° C. to a solution of 583 mg (2.87 mmol) of 3-(5-ethyl-1,3-oxazol-2-yl)phenyl methyl ether (Example 41A) in 13 ml of dichloromethane. After 1 h, the cooling bath is removed and the mixture is stirred at 25° C. for 4 h. At 0° C., firstly 25 ml of water and then 80 ml of ethyl acetate are added. The phases are separated, and the aqueous phase is extracted three times with 50 ml of ethyl acetate each time. After drying of the combined organic phases over MgSO$_4$ and filtration, the solvent is distilled off under reduced pressure. The residue is purified by chromatography on silica gel (0.04–0.063 mm) with dichloromethane/methanol 25:1 as mobile phase.

Yield: 550.3 mg (87.1% of theory) R$_f$(dichloromethane/methanol 20:1)=0.42 MS (DCI): 190 (M+H) HPLC, retention time=3.80 min $^1$H-NMR (300 MHz, DMSO-d$_6$): δ=1.20 (t, 3 H), 2.47–2.58 (m, 2 H), 6.89 (ddd, 1 H), 7.25–7.42 (m, 3 H), 7.88 (s, 1 H), 9.77 (s, 1 H).

The phenols in Table 2A were obtained by the process described for Example 45A.

TABLE 2A

| Example | Structure | Starting compound | Yield [%] | HPLC ($t_{ret}$) [min] | MS (DCI) [m/z] |
|---|---|---|---|---|---|
| 46A | ![structure] | 42A | 64.0 | 4.1 | 247 (M + NH$_4$) |
| 47A | ![structure] | 43A | 46.3 | 3.47 | 192 (M + H) |
| 48A | ![structure] | 44A | 97.3 | 3.83 | 229 (M + H)<br>246 (M + NH$_4$) |

PREPARATION EXAMPLES

EXAMPLE 1
3'-Chloro[1,1'-biphenyl]-3-yl 4,4,4-trifluoro-1-butanesulfonate

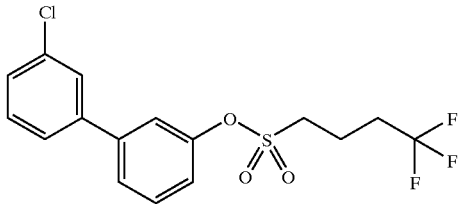

84.00 mg (0.41 mmol) of 3-(3-chlorophenyl)phenol from Example 1A are introduced at 0° C. into 1.0 ml of dichloromethane, and 66.15 mg (0.205 mmol) of tetrabutylammonium bromide and 0.0613 ml of 45 percent strength sodium hydroxide solution are added. After dropwise addition of a solution of 103.7 mg (0.49 mmol) of 4,4,4-trifluorobutanesulfonyl chloride (WO-A-98/37061, page 131) in 1 ml of dichloromethane, the mixture is stirred at 25° C. for 1.5 hours. The reaction mixture is mixed with 1 ml of water and filtered through a cartridge packed with 3 g of Extrelut® NT3 (Merck) and thoroughly washed with dichloromethane, and the solvent is distilled off under reduced pressure. The residue is purified by chromatography on silica gel (0.04–0.063 mm) with cyclohexane/dichloromethane 1/1 as mobile phase.

Yield: 142.3 mg (90.2% of theory) R$_f$(cyclohexane/dichloromethane 1/1)=0.20 MS (EI): 379 (M+H) HPLC, retention time=5.14 min $^1$H-NMR(300 MHz, DMSO-d$_6$): δ=2.01 (m, 2H), 2.50 (m, 2H), 3.75 (t, 2H), 7.3–7.9 (m, 8H).

The compounds in Table 2 were obtained by the process described for Example 1:

TABLE 2

| Example | Structure | Starting compound | Yield [%] | MS (EI) [m/z] | HPLC ($T_{ret}$) [min] |
|---|---|---|---|---|---|
| 2 | ![structure] | 2A | 96.13 | 413 (M + H) | 5.3 |

TABLE 2-continued

| Example | Structure | Starting compound | Yield [%] | MS (EI) [m/z] | HPLC (T_ret) [min] |
|---|---|---|---|---|---|
| 3 | 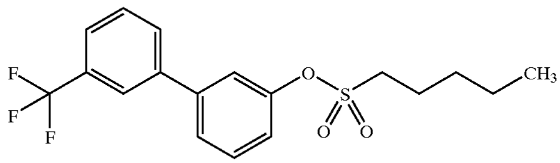 | 2A | 98.83 | 373 (M + H) | 5.55 |
| 4 | 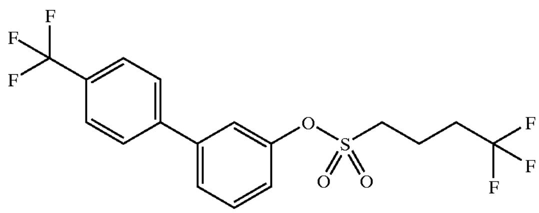 | 3A | 94.49 | 413 (M + H) | 5.2 |
| 5 | 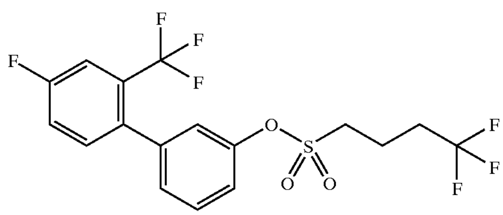 | 5A | 93.01 | 431 (M + H) | 5.12 |
| 6 | 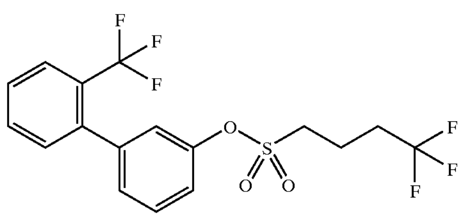 | 6A | 92.94 | 413 (M + H) | 5.07 |
| 7 | 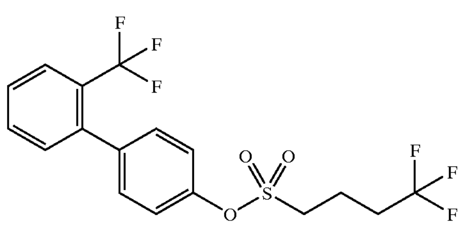 | 7A | 95.32 | 413 (M + H) | 5.09 |
| 8 | 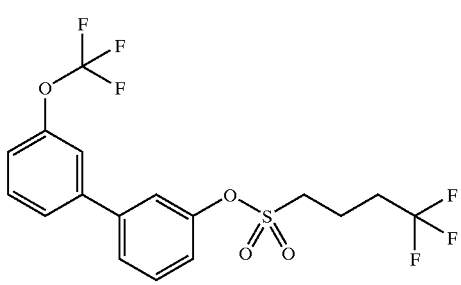 | 8A | 94.12 | 429 (M + H) | 5.24 |

TABLE 2-continued

| Example | Structure | Starting compound | Yield [%] | MS (EI) [m/z] | HPLC (T$_{ret}$) [min] |
|---|---|---|---|---|---|
| 9 | 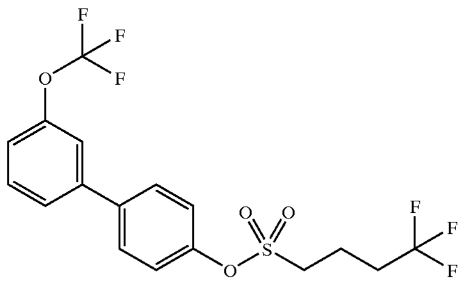 | 9A | 94.23 | 429 (M + H) | 5.26 |
| 10 | 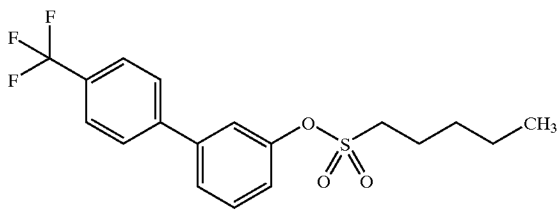 | 3A | 96.85 | 373 (M + H) | 5.44 |
| 11 | 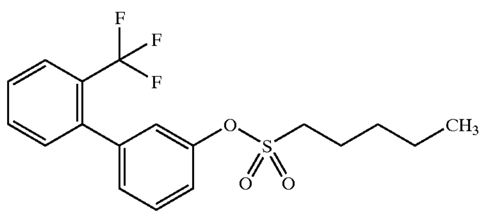 | 6A | 94.51 | 373 (M + H) | 5.31 |
| 12 | 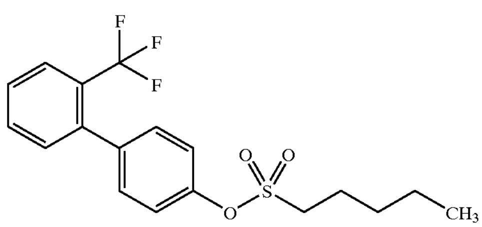 | 7A | 93.79 | 373 (M + H) | 5.33 |
| 13 | 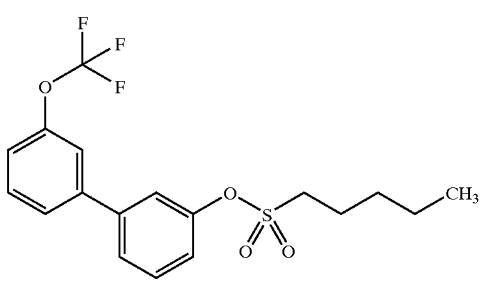 | 8A | 94.82 | 389 (M + H) | 5.49 |
| 14 | 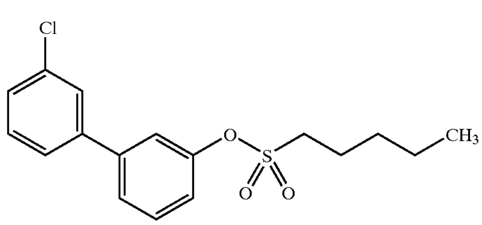 | 10A | 89.8 | 339 (M + H) | 5.42 |

TABLE 2-continued

| Example | Structure | Starting compound | Yield [%] | MS (EI) [m/z] | HPLC (T_ret) [min] |
|---|---|---|---|---|---|
| 15 | 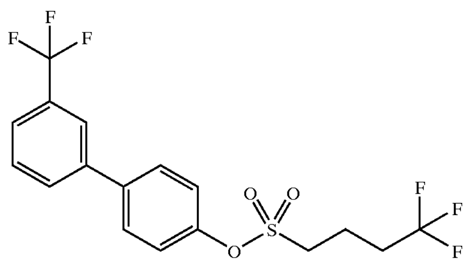 | 12A | 92.81 | 413 (M + H) | 5.18 |
| 16 | 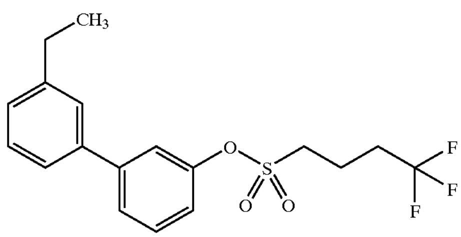 | 13A | 81.01 | 373 (M + H) | 5.28 |
| 17 | 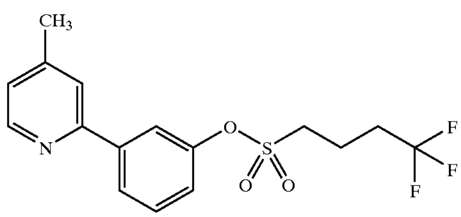 | 11A | 68.92 | 360 (M + H) | 3.86 |
| 18 | 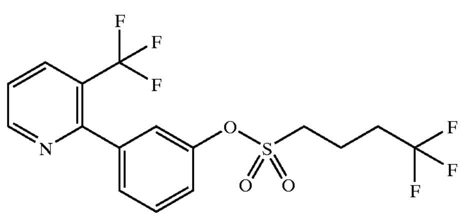 | 14A | 83.51 | 414 (M + H) | 4.63 |
| 19 | 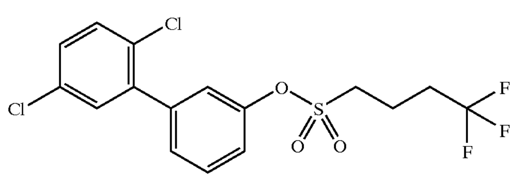 | 15A | 87.23 | 414 (M + H) | 5.25 |
| 20 | 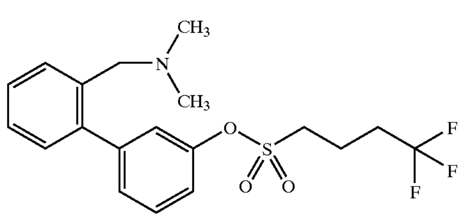 | 16A | 73.21 | ESI 402 (M + H) | 3.59 |

TABLE 2-continued

| Example | Structure | Starting compound | Yield [%] | MS (EI) [m/z] | HPLC (T_ret) [min] |
|---|---|---|---|---|---|
| 21 | 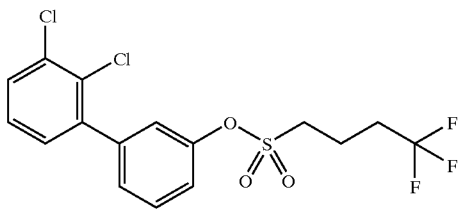 | 17A | 86.99 | 414 (M + H) | 5.21 |
| 22 | 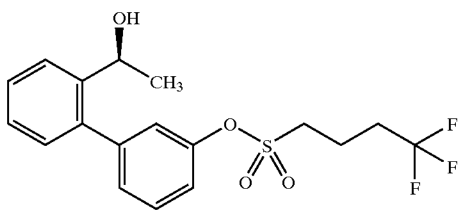 | 18A | 57.2 | 389 (M + H) | 4.54 |
| 23 | 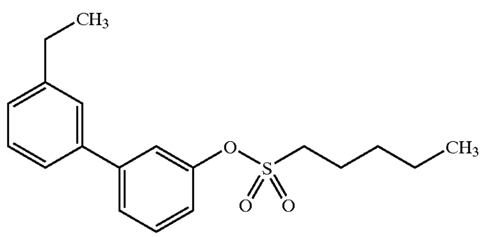 | 13A | 74.45 | 333 (M + H) | 5.56 |
| 24 | 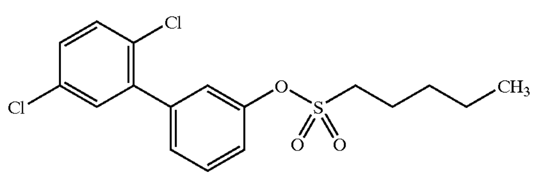 | 15A | 81.92 | 374 (M + H) | 5.53 |
| 25 | 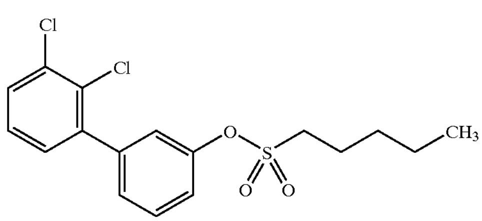 | 17A | 85.57 | 374 (M + H) | 5.49 |
| 26 | 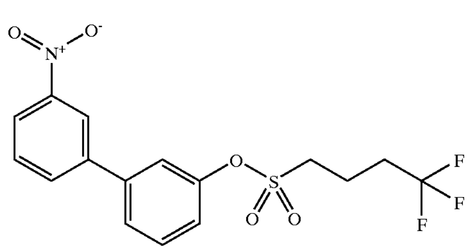 | 19A | 90.63 | 391 (M + H) | 4.85 |

TABLE 2-continued

| Example | Structure | Starting compound | Yield [%] | MS (EI) [m/z] | HPLC (T_ret) [min] |
|---|---|---|---|---|---|
| 27 | 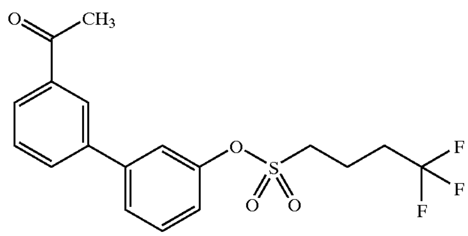 | 20A | 67.4 | 388 (M + H) | 4.7 |
| 28 | 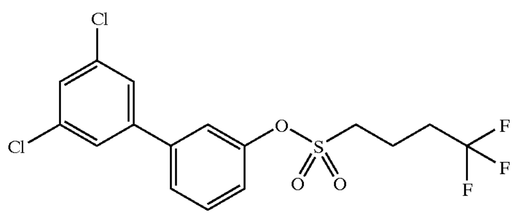 | 21A | 84.04 | 415 (M + H) | 5.46 |
| 29 | 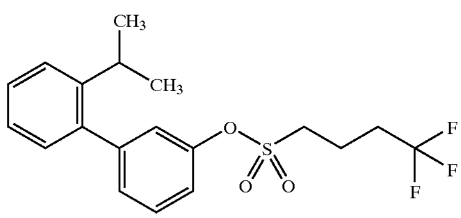 | 23A | 83.92 | 388 (M + H) | 5.38 |
| 30 | 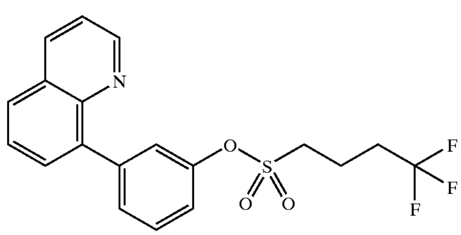 | 24A | 81.62 | 397 (M + H) | 4.51 |
| 31 | 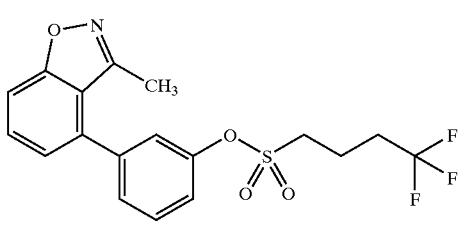 | 25A | 64.05 | 401 (M + H) | 4.83 |
| 32 | 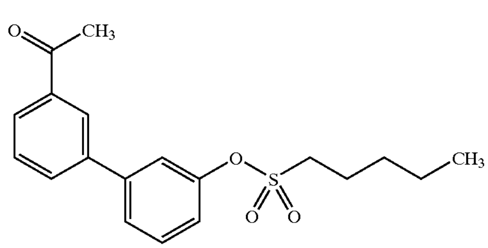 | 20A | 67.75 | 348 (M + H) | 4.92 |

TABLE 2-continued

| Example | Structure | Starting compound | Yield [%] | MS (EI) [m/z] | HPLC (T_ret) [min] |
|---|---|---|---|---|---|
| 33 | 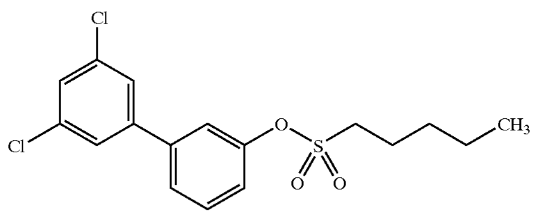 | 21A | 83.09 | 375 (M + H) | 5.77 |
| 34 | 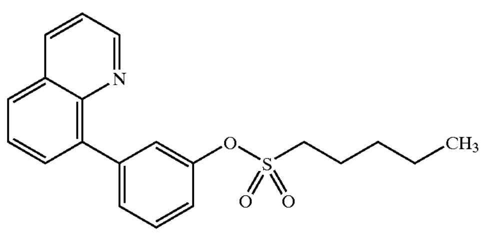 | 24A | 75.18 | 357 (M + H) | 4.75 |
| 35 | 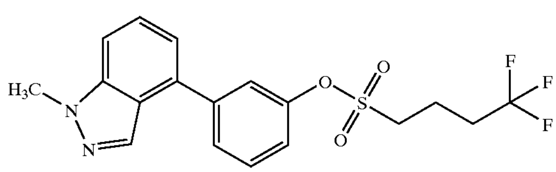 | 26A | 70.69 | (DCI, NH$_3$) 399 (M + H) | 4.68 |
| 36 | 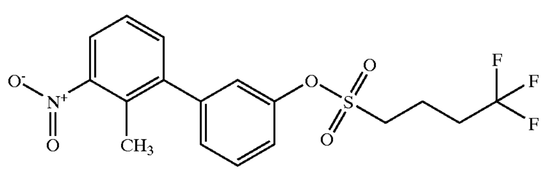 | 27A | 73.59 | (DCI, NH$_3$) 421 (M + NH$_4$) | 4.93 |
| 37 | 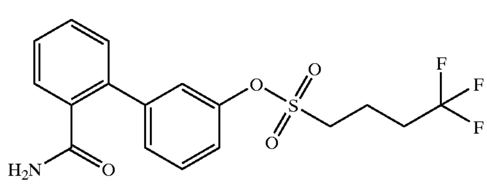 | 28A | 66.4 | (DCI, NH$_3$) 405 (m + NH$_4$) | 4.38 |
| 38 | 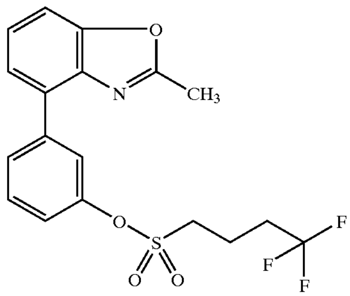 | 29A | 82.25 | (DCI, NH$_3$) 400 (M + H) | 4.88 |

TABLE 2-continued

| Example | Structure | Starting compound | Yield [%] | MS (EI) [m/z] | HPLC ($T_{ret}$) [min] |
|---|---|---|---|---|---|
| 39 | 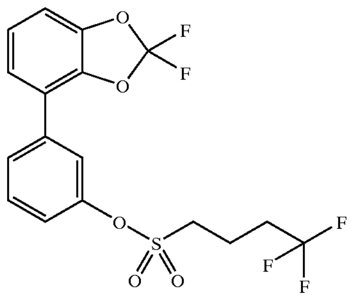 | 30A | 84.03 | (DCI, $NH_3$) 441 (M + $NH_4$) | 5.16 |
| 40 | 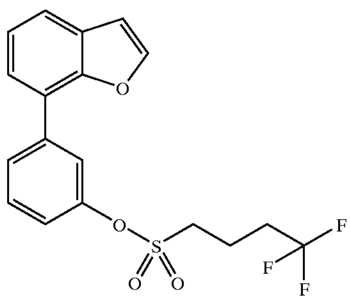 | 31A | 87.5 | (DCI, $NH_3$) 402 (M + $NH_4$) | 5.01 |
| 41 | 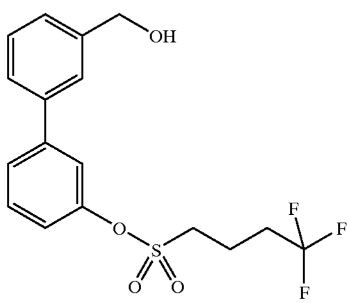 | 32A | 24.99 | (DCI, $NH_3$) 374 (M + $NH_4$) | 4.38 |
| 42 | 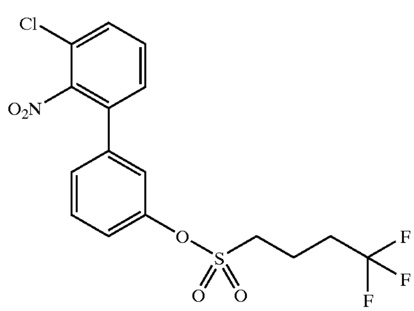 | 33A | 77.89 | ESI: 446 (M + Na) | 5.09 |
| 43 | 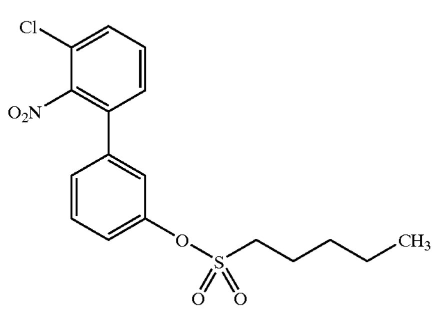 | 33A | 91.71 | ESI: 406 (M + Na) | 5.32 |

TABLE 2-continued

| Example | Structure | Starting compound | Yield [%] | MS (EI) [m/z] | HPLC (T$_{ret}$) [min] |
|---|---|---|---|---|---|
| 44 | (3-(dimethylamino)phenyl)phenyl 4,4,4-trifluorobutane-1-sulfonate | 34A | 79.35 | ESI: 388 (M + H) | 4.63 |
| 45 | (3-(dimethylamino)phenyl)phenyl pentane-1-sulfonate | 34A | 90.58 | ESI: 348 (M + H) | 4.91 |
| 46 | 3-(isoquinolin-5-yl)phenyl 4,4,4-trifluorobutane-1-sulfonate | 35A | 97.12 | ESI: 396 (M + H) | 3.84 |
| 47 | 3-(isoquinolin-5-yl)phenyl pentane-1-sulfonate | 35A | 92.83 | ESI: 356 (M + H) | 3.99 |

TABLE 2-continued

| Example | Structure | Starting compound | Yield [%] | MS (EI) [m/z] | HPLC ($T_{ret}$) [min] |
|---|---|---|---|---|---|
| 48 | 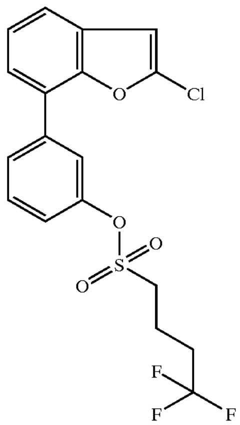 | 40[1] | 22.23 | ESI: 419 (M + H) | 5.41 |
| 49 | 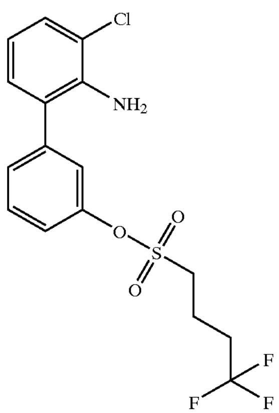 | 42[2] | 78.14 | ESI: 394 (M + H) | 4.96 |
| 50 | 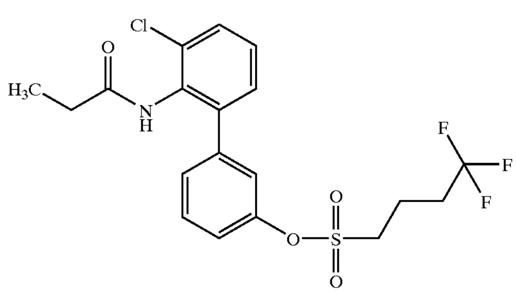 | 49[3] | 27.7 | ESI: 472 (M + Na) | 4.57 |
| 51 | 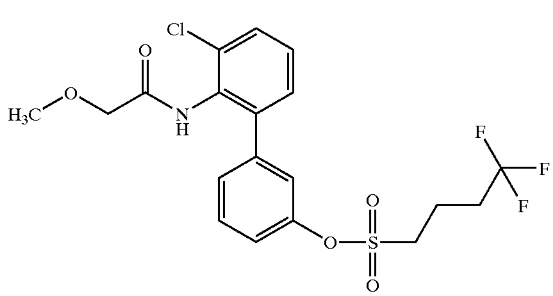 | 49[4] | 46.79 | ESI: 488 (M + Na) | 4.55 |

TABLE 2-continued

| Example | Structure | Starting compound | Yield [%] | MS (EI) [m/z] | HPLC (T$_{ret}$) [min] |
|---|---|---|---|---|---|
| 52 | 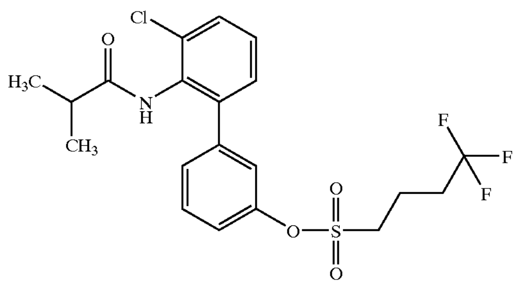 | 49[5)] | 32.43 | ESI: 464 (M + H) | 4.7 |
| 53 | 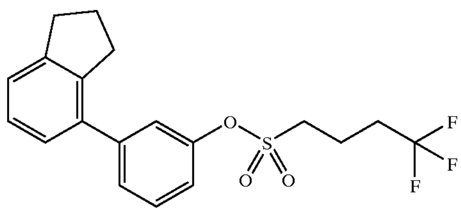 | 36A | 87.99 | (DCI, NH$_3$) 402 (M + NH$_4$) | 5.57 |
| 54 | 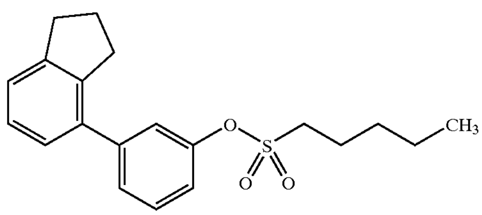 | 36A | 91.68 | (DCI, NH$_3$) 362 (M + NH$_4$) | 5.89 |
| 55 | 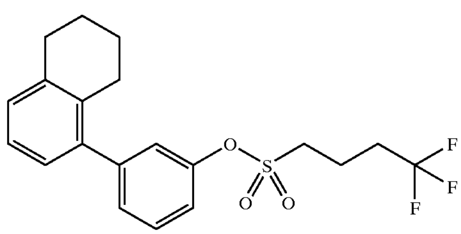 | 37A | 87.26 | (DCI, NH$_3$) 416 (M + NH$_4$) | 5.67 |
| 56 | 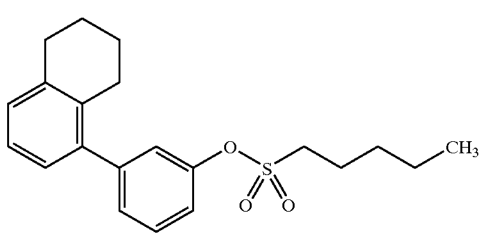 | 37A | 88.53 | (DCI, NH$_3$) 376 (M + NH$_4$) | 6.04 |
| 57 | 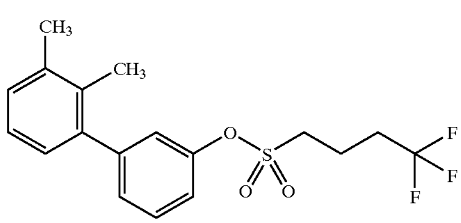 | 38A | 84.08 | (DCI, NH$_3$) 390 (M + NH$_4$) | 5.4 |

TABLE 2-continued

| Example | Structure | Starting compound | Yield [%] | MS (EI) [m/z] | HPLC ($T_{ret}$) [min] |
|---|---|---|---|---|---|
| 58 | ![structure] | 38A | 90.65 | (DCI, NH$_3$) 350 (M + NH$_4$) | 5.72 |

1) Prepared from Example 40 by reaction with N-chlorosuccinimide in DMF at 100° C.
2) Prepared from Example 42 by reaction with iron powder in glacial acetic acid/water at 90° C.
3) Prepared from Example 49 by reaction with propionyl chloride in pyridine under reflux
4) Prepared from Example 49 by reaction with methoxyacetyl chloride in pyridine under reflux
5) Prepared from Example 49 by reaction with butyryl chloride in pyridine under reflux

EXAMPLE 59

2-(4-tert-Butylphenyl)-4-pyridinyl 4,4,4-trifluoro-1-butanesulfonate

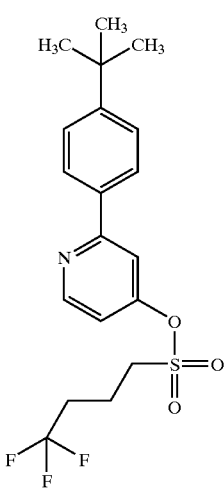

42.2 mg (0.24 mmol) of 4-tert-butylbenzeneboronic acid, 90 mg (0.22 mmol) of 2-trifluoromethylsulfonyloxy-4-pyridinyl 4,4,4-trifluoro-1-butanesulfonate (Example 40A), 12.5 mg (0.01 mmol) of tetrakisphenylpalladium(0) and 68.6 mg (0.65 mmol) of sodium carbonate are heated in 5 ml of dioxane at 80° C. under argon for 2 hours. The reaction mixture is cooled, mixed with 0.5 ml of water and filtered through a cartridge packed with 3 g of Extrelut NT3 (Merck) and thoroughly washed with dichloromethane, and the solvent is distilled off under reduced pressure. The residue is purified by preparative HPLC and chromatography on silica gel (toluene).

Yield: 15.4 mg (17.8% of theory) MS (EI): 402 (M+H) HPLC, retention time=5.47 min The compounds in Table 3 were obtained from Example 40A by the process described for Example 59:

TABLE 3

| Example | Structure | Starting compound | Yield [%] | MS (EI) [m/z] | HPLC ($t_{ret}$) [min] |
|---|---|---|---|---|---|
| 60 | 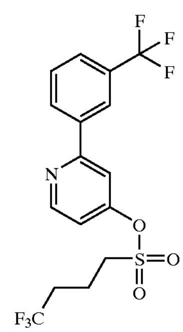 | 40A | 9.8 | 414 (M + H) | 5.34 |
| 61 | 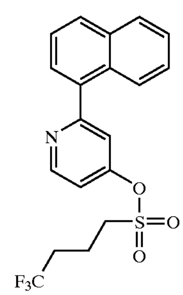 | 40A | 5 | 396 (M + H) | 4.89 |
| 62 | 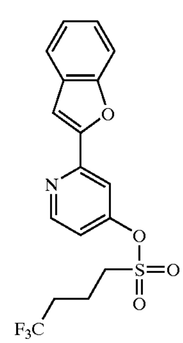 | 40A | 29.8 | 386 (M + H) | $R_f$ 0.40 cyclohexane/ ethyl acetate (9:1) |

EXAMPLE 63
3-(4-Ethyl-1,3-oxazol-2-yl)phenyl 4,4,4-trifluoro-1-butanesulfonate

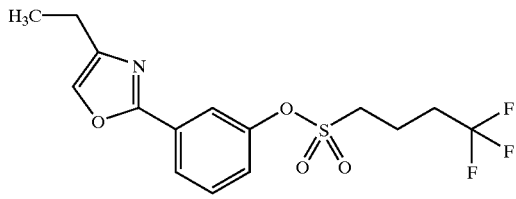

1.66 ml (6.34 mmol) of tetrabutylammonium hydroxide (40% strength aqueous solution) are added to 200 mg (1.06 mmol) of 3-(4-ethyl-1,3-oxazol-2-yl)phenol from Example 45A in dichloromethane (7.0 ml). After 5 minutes, 333.9 mg (1.59 mmol) of 4,4,4-trifluorobutanesulfonyl chloride are added and the mixture is stirred at 25° C. for 2 hours. 5 ml of water are added to the reaction mixture, and the aqueous phase is extracted three times with 25 ml of dichloromethane each time. The combined organic phases are dried over $Na_2SO_4$ and, after filtration, the solvent is distilled off under reduced pressure. The residue is purified by chromatography on silica gel (0.04–0.063 mm) with dichloromethane/ethyl acetate 100:1/50:1 as mobile phase.

Yield: 210.2 mg (53.8% of theory) $R_f$(cyclohexane/ethyl acetate 3:1)=0.34 MS (EI): 363 HPLC, retention time=4.88 min $^1$H-NMR (300 MHz, $CDCl_3$): δ=1.29 (t, 3 H), 2.20–2.52 (m, 4 H), 2.63 (q, 2 H), 3.39 (t, 2 H), 7.30–7.58 (m, 3 H), 7.90 (d, 1 H), 7.99 (br. d, 1 H).

The compounds in Table 4 are obtained by the process described for Example 63:

The abovementioned examples show the following $^1$H-NMR spectroscopic data:

TABLE 5

| Example | |
|---|---|
| 2 | $^1$H-NMR (300 MHz, DMSO-$d_6$): δ/ppm = 2.00–2.15 (m, 2H), 2.40–2.60 (m, 2H), 3.74 (t, J = 7.5 Hz, 2H), 7.35–8.10 (m, 8H) |
| 8 | $^1$H-NMR (200 MHz, DMSO-$d_6$): δ/ppm = 1.95–2.20 (m, 2H), 2.35–2.65 (m, 2H), 3.73 (t, J = 7.5 Hz, 2H), 7.32–7.87 (m, 8H) |
| 21 | $^1$H-NMR (200 MHz, DMSO-$d_6$): δ/ppm = 1.90–2.20 (m, 2H), 2.33–2.67 (m, 2H), 3.71 (t, J = 7.5 Hz, 2H), 7.35–7.80 (m, 8H) |
| 53 | $^1$H-NMR (200 MHz, DMSO-$d_6$): δ/ppm = 1.86–2.20 (m, 4H), 2.35–2.65 (m, 2H), 2.75–3.05 (m, 4H), 3.71 (t, J = 7.5 Hz, 2H), 7.15–7.75 (m, 7H) |
| 55 | $^1$H-NMR (200 MHz, DMSO-$d_6$): δ/ppm = 1.50–1.85 (m, 4H), 1.90–2.13 (m, 2H), 2.35–2.60 (m, 4H), 2.70–2.90 (t, J = 6 Hz, 2H), 3.69 (t, J = 7.5 Hz, 2H), 6.90–7.62 (m, 7H) |

What is claimed is:
1. A compound of the formula (I),

A-D-O—$SO_2$—$R^1$   (I)

in which
A represents ($C_6$–$C_{10}$)-aryl,
where adjacent ring atoms in the aryl are optionally connected by a saturated or partially unsaturated bridge comprising 3 to 7 bridge atoms selected from the group of carbon, nitrogen, oxygen and sulphur, and
where the aryl and the bridge are optionally substituted one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl,

TABLE 4

| Example | Structure | Starting compound | Yield [%] | HPLC ($t_{ret}$) [mm] | MS (EI) [m/z] |
|---|---|---|---|---|---|
| 64 | 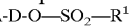 | 46A | 44.3 | 5.26 | 364 (M + H) |
| 65 | 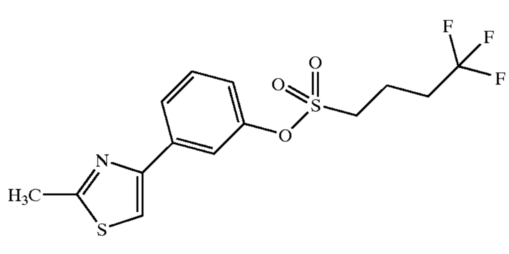 | 47A | 75.0 | 4.77 | 365 |
| 66 | 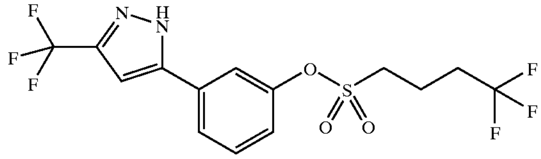 | 48A | 49.4 | 4.70 | 403 (M + H) |

($C_3$–$C_8$)-cycloalkyl, halogen, nitro, cyano, hydroxyl, trifluoromethoxy, —$CO_2R^2$, —$CONR^3R^4$, —$SO_2NR^5R^6$, —$NR^7COR^8$, —$NR^9SO_2R^{10}$ and —$NR^{11}R^{12}$, where ($C_1$–$C_8$)-alkyl in turn is optionally substituted by halogen, cyano, hydroxyl or —$NR^{13}R^{14}$, in which $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are identical or different and denote hydrogen, optionally hydroxyl- or ($C_1$–$C_4$)-alkoxy-substituted ($C_1$–$C_8$)-alkyl or ($C_3$–$C_8$)-cycloalkyl, D represents ($C_6$–$C_{10}$)-arylene where the arylene is optionally substituted one or more times by radicals selected from the group of ($C_1$–$C_8$)-alkyl, ($C_2$–$C_8$)-alkenyl, ($C_2$–$C_8$)-alkinyl, ($C_1$–$C_8$)-alkoxy, ($C_1$–$C_8$)-alkanoyl, ($C_3$–$C_8$)-cycloalkyl, halogen, nitro, cyano, hydroxyl, trifluoromethyl, trifluoromethoxy and —$CO_2R^{15}$, in which $R^{15}$ denotes hydrogen, ($C_1$–$C_8$)-alkyl or ($C_3$–$C_8$)-cycloalkyl, and $R^1$ represents ($C_4$–$C_8$)-alkyl, represents ($C_2$–$C_8$)-alkyl where the carbon chain is interrupted by one or two heteroatoms or groups selected from the group of —O—, —S—, —SO— and —$SO_2$—, or represents ($C_2$–$C_8$)-alkinyl, where alkyl and alkinyl are optionally substituted one or more times by halogen and/or cyano, and the salts, hydrates or solvates thereof, with the exception of compounds of the general formula (I), in which D is phenylene and $R^1$ is nonafluorobutyl, and with the exception of biphenyl-4-yl-heptadecafluoro-1-octanesulphonate and biphenyl-2-yl-heptadecafluoro-1-octanesulphonate.

2. A compound as claimed in claim 1, in which

A represents ($C_6$–$C_{10}$)-aryl, where adjacent ring atoms in the aryl are optionally connected by a saturated bridge comprising 3 to 5 bridge carbon atoms, and where the aryl and the bridge are optionally substituted one to three times by radicals selected from the group of ($C_1$–$C_6$)-alkyl, ($C_1$–$C_6$)-alkoxy, ($C_1$–$C_6$)-alkanoyl, halogen, nitro, cyano, hydroxyl, trifluoromethoxy, —$CONR^3R^4$, —$NR^7COR^8$, and —$NR^{11}R^{12}$, where ($C_1$–$C_6$)-alkyl in turn is optionally substituted by halogen, hydroxyl or —$NR^{13}R^{14}$, in which $R^3$, $R^4$, $R^7$, $R^8$, $R^{11}$, $R^{12}$, $R^{13}$ and $R^{14}$ are identical or different and denote hydrogen, optionally hydroxyl- or ($C_1$–$C_4$)-alkoxy-substituted ($C_1$–$C_6$)-alkyl or ($C_3$–$C_8$)-cycloalkyl, D represents phenylene, where phenylene is optionally substituted one to three times by radicals from the group of ($C_1$–$C_4$)-alkyl, ($C_1$–$C_4$)-alkoxy, halogen, nitro, cyano, trifluoromethyl and trifluoromethoxy, and $R^1$ represents, where appropriate, partially fluorinated ($C_4$–$C_8$)-alkyl, and the salts, hydrates or solvates thereof.

3. A compound as claimed in claim 1, where

A represents phenyl, indanyl or 1,2,3,4-tetrahydronaphthyl, where the rings are optionally substituted one to three times by radicals selected from the group of($C_1$–$C_4$)-alkyl, halogen, cyano, trifluoromethyl and trifluoromethoxy, D represents 1,3-phenylene, where the phenylene is optionally substituted up to twice by radicals selected from the group of ($C_1$–$C_4$)-alkyl, halogen, cyano, trifluoromethyl and trifluoromethoxy, and $R^1$ represents 4,4,4-trifluorobut-1-yl or n-pentyl, and the salts, hydrates or solvates thereof.

4. A process for the preparation of a compound as claimed in claim 1, characterized in that

[A] a compound of the general formula (II)

$$A\text{-}D\text{-}OH \tag{II}$$

in which

A and D have the meaning indicated in claim 1, is reacted in an inert solvent in the presence of a suitable base with a compound of the general formula (III), $$X^1\text{—}SO_2\text{—}R^1 \tag{III}$$

in which $X^1$ represents a suitable leaving group, and $R^1$ has the meaning indicated in claim 1, or,

[B] a compound of the general formula (IV)

$$A\text{-}X^2 \tag{IV}$$

in which

A has the meaning indicated in claim 1, and $X^2$ represents a radical selected from the group of —$B(OR^{16})_2$, —$SnR^{17}_3$, —$ZnR^{18}$ and —$SiR^{19}Cl_2$, in which $R^{16}$ represents hydrogen or ($C_1$–$C_6$)-alkyl, or two $R^{16}$ radicals together denote ($C_2$–$C_6$)-alkanediyl or benzene-1,2-diyl, and $R^{17}$, $R^{18}$ and $R^{19}$ denote ($C_1$–$C_6$)-alkyl, is reacted in an inert solvent in the presence of a palladium catalyst and of a base with a compound of the general formula (V)

$$X^3\text{-}D\text{-}O\text{—}SO_2\text{—}R^1 \tag{V}$$

in which $X^3$ is a suitable leaving group, and

D and $R^1$ have the meaning indicated in claim 1.

* * * * *